United States Patent
DeKelver et al.

(10) Patent No.: US 9,914,940 B2
(45) Date of Patent: Mar. 13, 2018

(54) TARGETED INTEGRATION INTO THE PPP1R12C LOCUS

(71) Applicant: Sangamo BioSciences, Inc., Richmond, CA (US)

(72) Inventors: Russell DeKelver, Richmond, CA (US); Philip D. Gregory, Richmond, CA (US); David Paschon, Richmond, CA (US); Phillip Tam, Richmond, CA (US); Fyodor Urnov, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 0 days.

(21) Appl. No.: 15/014,372

(22) Filed: Feb. 3, 2016

(65) Prior Publication Data

US 2016/0289699 A1 Oct. 6, 2016

Related U.S. Application Data

(63) Continuation of application No. 14/447,378, filed on Jul. 30, 2014, now Pat. No. 9,267,154, which is a continuation of application No. 13/341,228, filed on Dec. 30, 2011, now Pat. No. 8,822,221, which is a continuation of application No. 12/150,103, filed on Apr. 24, 2008, now Pat. No. 8,110,379.

(60) Provisional application No. 60/926,322, filed on Apr. 26, 2007.

(51) Int. Cl.
| | |
|---|---|
| *C12N 15/11* | (2006.01) |
| *C12N 15/90* | (2006.01) |
| *C12N 15/10* | (2006.01) |
| *C07K 14/435* | (2006.01) |
| *C12N 9/22* | (2006.01) |
| *C12N 15/113* | (2010.01) |

(52) U.S. Cl.
CPC .......... *C12N 15/907* (2013.01); *C07K 14/435* (2013.01); *C07K 14/43595* (2013.01); *C12N 9/22* (2013.01); *C12N 15/1082* (2013.01); *C12N 15/113* (2013.01); *C12Y 301/21004* (2013.01); *C07K 2319/81* (2013.01); *C12N 2800/10* (2013.01); *C12N 2800/30* (2013.01)

(58) Field of Classification Search
None
See application file for complete search history.

(56) References Cited

U.S. PATENT DOCUMENTS

| | | | |
|---|---|---|---|
| 5,356,802 A | 10/1994 | Chandrasegaran | |
| 5,436,150 A | 7/1995 | Chandrasegaran | |
| 5,487,994 A | 1/1996 | Chandrasegaran | |
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas et al. | |
| 6,200,759 B1 | 3/2001 | Dove et al. | |
| 6,242,568 B1 | 6/2001 | Barbas et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,534,261 B1 | 3/2003 | Cox et al. | |
| 2003/0232410 A1 | 12/2003 | Liljedahl et al. | |
| 2005/0026157 A1 | 2/2005 | Baltimore | |
| 2005/0064474 A1 | 3/2005 | Urnov et al. | |
| 2005/0208489 A1 | 9/2005 | Carroll | |
| 2006/0063231 A1 | 3/2006 | Li et al. | |
| 2006/0188987 A1 | 8/2006 | Guschin et al. | |

FOREIGN PATENT DOCUMENTS

| | | |
|---|---|---|
| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/053480 A1 | 7/2001 |
| WO | WO 01/060970 A2 | 8/2001 |
| WO | 01/088197 A2 | 11/2001 |
| WO | 02/016536 A1 | 2/2002 |
| WO | 02/057293 A2 | 7/2002 |
| WO | 02/077227 A2 | 10/2002 |
| WO | 02/099084 A2 | 12/2002 |
| WO | 03/016496 A2 | 2/2003 |
| WO | 2006/121579 A2 | 11/2006 |
| WO | 07/014275 A2 | 1/2007 |
| WO | 07/139898 A2 | 12/2007 |

OTHER PUBLICATIONS

Durai, et al., "Zinc Finger Nucleases: Custom-Designed Molecular Scissors for Genome Engineering of Plant and Mammalian Cells," *Nucleic Acids Research* 33(18):5978-5990 (2005).
Bitinate, et al., "FokI Dimerization Is Required for DNA Cleavage," *PNAS USA* 95:10570-10575 (1998).
Cathomen, et al., "Zinc-Finger Nucleases: The Next Generation Emerges," *Molecular Therapy* 16:1200-1207 (2008).
Choulika, et al., "Induction of Homologous Recombination in Mammalian Chromosomes by Using the I-SCEI System of *Saccharomyces cerevisiae*," *Mol. Cell. Biol.* 15:1968-1973 (1995).
Donoho, et al., "Analysis of Gene Targeting and Intrachromosomal Homologous Recombination Stimulated by Genomic Double-Strand Breaks in Mouse Embryonic Stem Cells," *Mol. And Cell. Biol.* 18: 4070-4078 (1998).

(Continued)

*Primary Examiner* — Celine X Qian
(74) *Attorney, Agent, or Firm* — Pasternak Patent Law; Susan Abrahamson

(57) ABSTRACT

Disclosed herein are methods and compositions for targeted integration of an exogenous sequence into the human PPP1R12C locus, for example, for expression of a polypeptide of interest.

20 Claims, 12 Drawing Sheets

(56) References Cited

OTHER PUBLICATIONS

Greisman, et al., "A General Strategy for Selecting High-Affinity Zinc Finger Proteins for Diverse DNA Target Sites," *Science* 275:657-661 (1997).
Hamilton, et al., "Adeno-Associaied Virus Site-Specific Integration and AAVS1 Disruption," *Journal of Virology* 78:7874-7882 (2004).
Kim, et al., "Chimeric Restriction Endonuclease," *PNAS USA* 91:883-887 (1994).
Kim, et al., "Insertion and Deletion Mutants of Foki Restriction Endonuclease," *J. Biol. Chem.* 269:31978-31981 (1994).
Li, et al., "Functional Domains in FOK I Restriction Endonuclease," *PNAS USA* 89:4275-4279 (1992).
Li, et al., "Alteration of the Cleavage Distance of FOK I Restriction Endonuclease by Insertion Mutagenesis," *PNAS USA* 90:2764-2768 (1993).
Miller, et al., "An Improved Zinc-Finger Nuclease Architecture for Highly Specific Genome Editing," *Nat Biotechnology* 25:778-785 (2007).
Moehle, et al., "Targeted Gene Addition Into a Specified Location in the Human Genome Using Designed Zinc Finger Nucleases," *PNAS* 104:3055-3060 (2007).
Moore, et al., "Design of Polyzinc Finger Peptides With Structured Linkers," *PNAS USA* 98:1432-1436 (2001).
Moore, et al., "Improved DNA Binding Specificity From Polyzinc Finger Peptides by Using Strings of Two-Finger Units," *PNAS USA* 98:1437-1441 (2001).
Porteus, et al., "Gene Targeting Using Zinc Finger Nucleases," *Nature Biotechnology* 23:967-973 (2005).
Rebar, et al., "Zinc Finger Phage: Affinity Selection of Fingers With New DNA-Binding Specifities," *Science* 263:671-673 (1994).
Rouet, et al., "Introduction of Double-Strand Breaks Into the Genome of Mouse Cells by Expression of a Rare-Cutting Endonuclease," *Molecular and Cellular Biology* 14:8096-8106 (1994).
Urnov, et al., "Highly Efficient Endogenous Human Gene Correction Using Designed Zinc-Finger Nucleases," *Nature* 435:646-651 (2005).
Warrington Jr., et al., "Treatment of Human Disease by Adeno-Associated Viral Gene Transfer," *Hum. Genet.* 119:571-603 (2006).
Wu, et al., "Custom-Designed Zinc Finger Nucleases: What Is Next?" *Cell Mol. Life Sci.* 64:2933-2944 (2007).

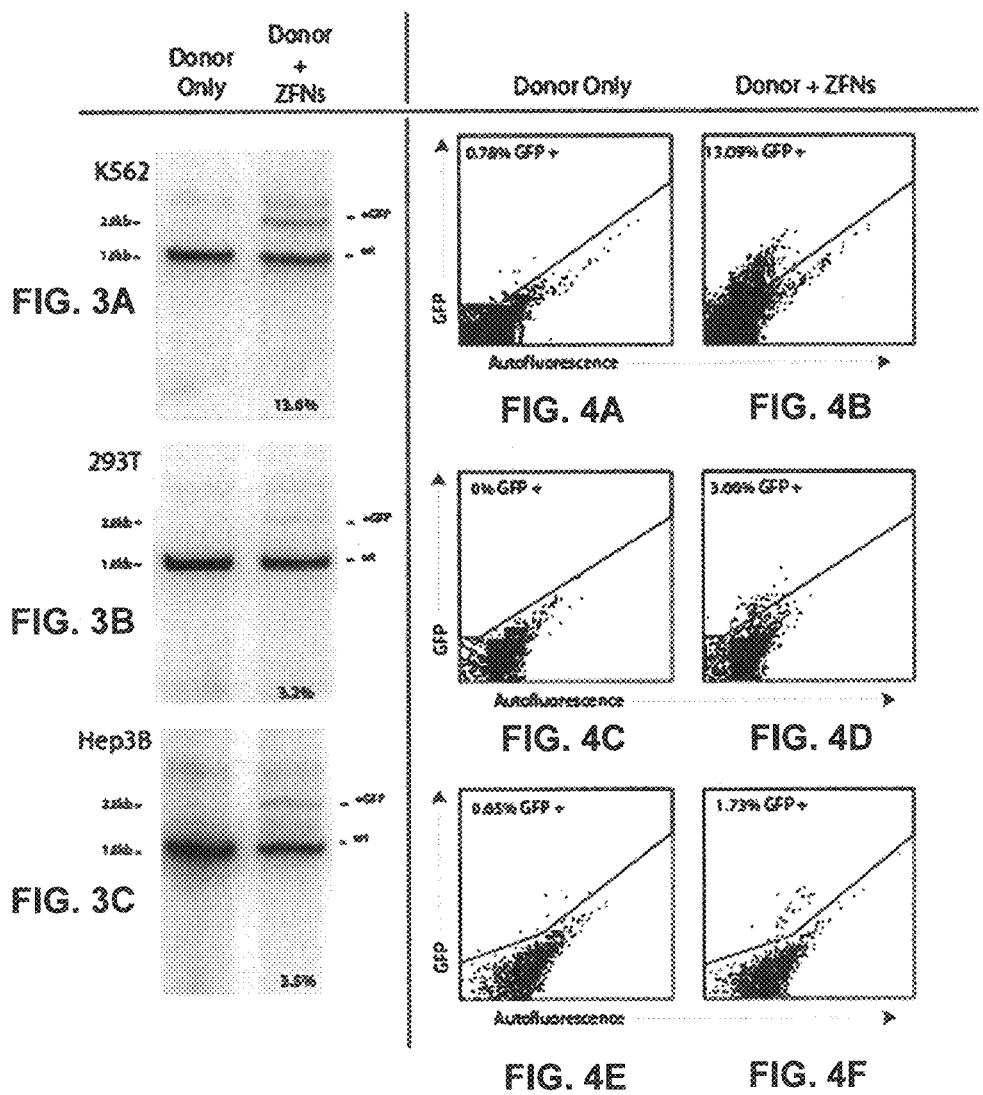

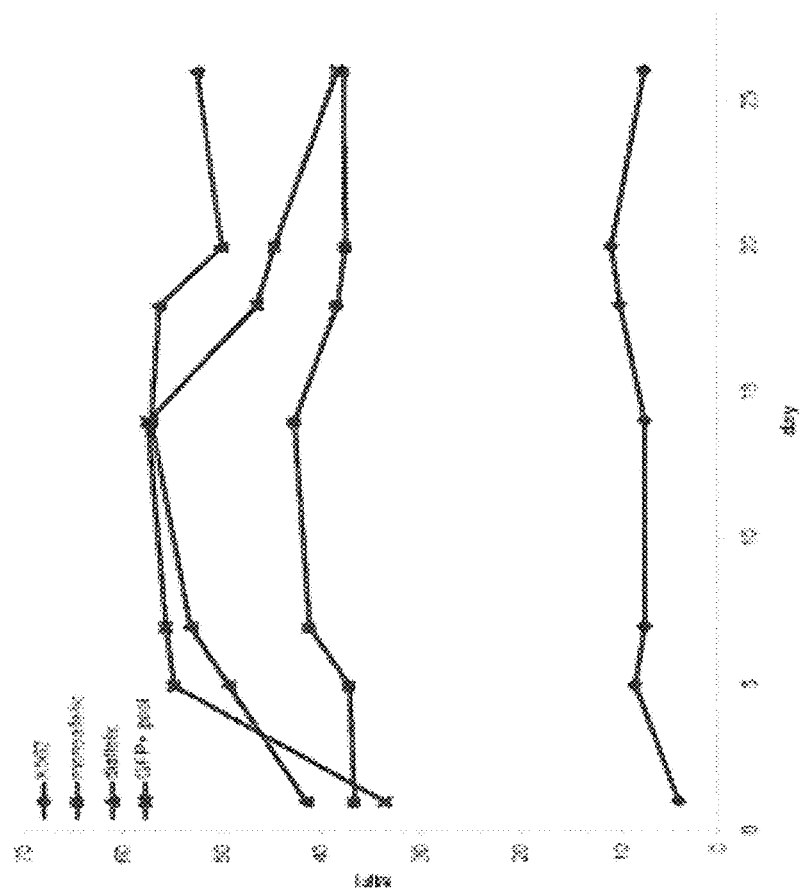

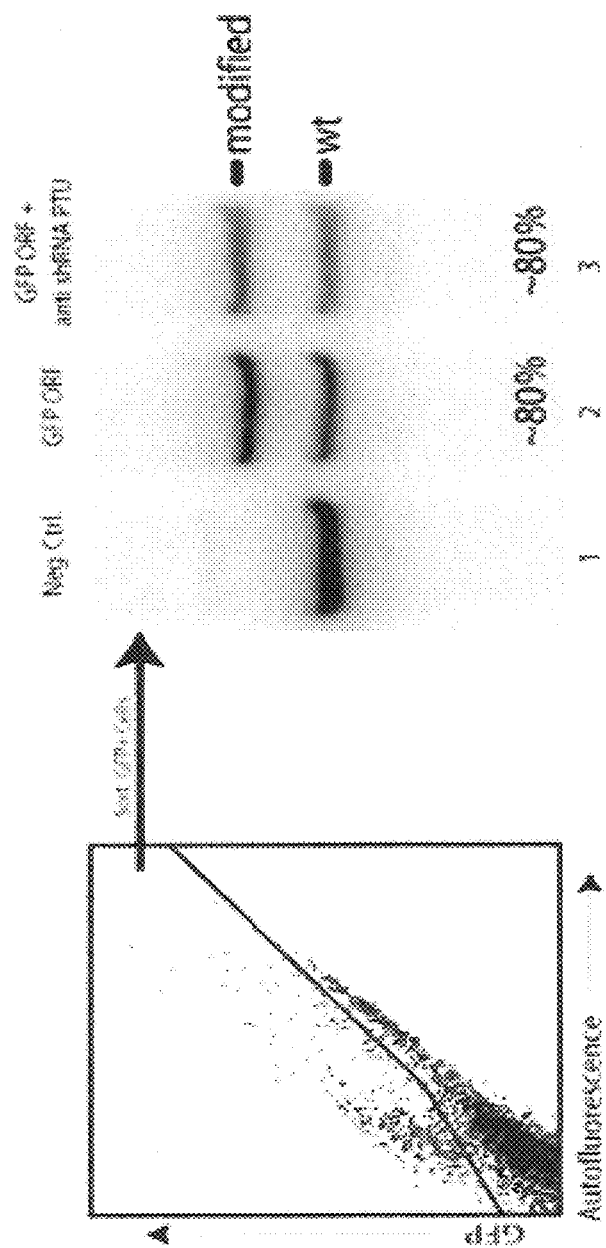

SEQUENCE LISTING

```
<160> NUMBER OF SEQ ID NOS: 19

<210> SEQ ID NO 1
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 1
actagggaca ggattg                                                  16

<210> SEQ ID NO 2
```

```
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 2
ccccactgtg gggtgg                                                    16

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

Gln Ser Ser Asn Leu Ala Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Arg Pro Asp Phe Leu Asn Gln
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Gln Ser Gly His Leu Ala Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Arg Ser Asp Asn Leu Thr Thr
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Gln Ser Ser His Leu Thr Arg
1               5

<210> SEQ ID NO 8
<211> LENGTH: 7
<212> TYPE: PRT
```

```
<213> ORGANISM: Artificial Sequence
<220> FEATURE:
<223> OTHER INFORMATION: Synthetic peptide

<400> SEQUENCE: 8

Arg Ser Asp His Leu Thr Thr
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

His Asn Tyr Ala Arg Asp Cys
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide

<400> SEQUENCE: 10

Gln Lys Ala Thr Arg Thr Thr
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

Arg Thr Asp Tyr Leu Val Asp
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Tyr Asn Thr His Leu Thr Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

Gln Gly Tyr Asn Leu Ala Gly
1               5

<210> SEQ ID NO 14
<211> LENGTH: 7
<212> TYPE: PRT
<213> ORGANISM: Artificial Sequence
```

```
<220> FEATURE:
<223> OTHER INFORMATION: Synthetic peptide

<400> SEQUENCE: 14

Glu Arg His His Leu Met Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Gln Asn Ser Thr Arg Ile Gly
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide

<400> SEQUENCE: 16

Tyr Asn Trp His Leu Gln Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Leu His His Gln Leu Val Arg
1               5

<210> SEQ ID NO 18
<211> LENGTH: 67
<212> TYPE: DNA
<213> ORGANISM: Artificial Sequence
<220> FEATURE:
<223> OTHER INFORMATION: Synthetic oligonucleotide

<400> SEQUENCE: 18
cttttatctg tccctccac cccacagtgg ggccactagg gacaggattg gtgacagaaa        60
agcccca                                                                 67

<210> SEQ ID NO 19
<211> LENGTH: 67
<212> TYPE: DNA
<213> ORGANISM: Artificial Sequence
<220> FEATURE:
<223> OTHER INFORMATION: Synthetic oligonucleotide

<400> SEQUENCE: 19
tggggctttt ctgtcaccaa tcctgtccct agtggcccca ctgtggggtg gaggggacag        60
ataaaag                                                                 67
```

TARGETED INTEGRATION INTO THE PPP1R12C LOCUS

CROSS-REFERENCE TO RELATED APPLICATIONS

The present application is a continuation of U.S. Ser. No. 14/447,378, filed Jul. 30, 2014, which is a continuation of U.S. patent application Ser. No. 13/341,228, filed Dec. 30, 2011 which is a continuation of U.S. patent application Ser. No. 12/150,103, filed Apr. 24, 2008, which claims the benefit of U.S. Provisional Application No. 60/926,322, filed Apr. 26, 2007, the disclosures of which are hereby incorporated by reference in their entireties.

STATEMENT OF RIGHTS TO INVENTIONS MADE UNDER FEDERALLY SPONSORED RESEARCH

Not applicable.

TECHNICAL FIELD

The present disclosure is in the field of genome engineering, particularly targeted integration into the human PPP1R12C ("p84" or "AAVS1") gene.

BACKGROUND

A major area of interest in genome biology, especially in light of the determination of the complete nucleotide sequences of a number of genomes, is targeted integration of one or more sequences of interest into desired locations. Attempts have been made to alter genomic sequences in cultured cells by taking advantage of the natural phenomenon of homologous recombination. See, for example, Capecchi (1989) *Science* 244:1288-1292; U.S. Pat. Nos. 6,528,313 and 6,528,314. If a polynucleotide has sufficient homology to the genomic region containing the sequence to be altered, it is possible for part or all of the sequence of the polynucleotide to replace the genomic sequence by homologous recombination. However, the frequency of homologous recombination under these circumstances is extremely low. Moreover, the frequency of insertion of the exogenous polynucleotide at genomic locations that lack sequence homology exceeds the frequency of targeted homologous recombination by several orders of magnitude. Sedivy and Joyner (1992) *Gene Targeting*, Oxford University Press, Oxford.

The introduction of a double-stranded break into genomic DNA, in the region of the genome bearing homology to an exogenous polynucleotide, has been shown to stimulate homologous recombination at this site by several thousand-fold in cultured cells. Rouet et al. (1994) *Mol. Cell. Biol.* 14:8096-8106; Choulika et al. (1995) *Mol. Cell. Biol.* 15:1968-1973; Donoho et al. (1998) *Mol. Cell. Biol.* 18:4070-4078. See also Johnson et al. (2001) *Biochem. Soc. Trans.* 29:196-201; and Yanez et al. (1998) *Gene Therapy* 5:149-159. In these methods, DNA cleavage in the desired genomic region was accomplished by inserting a recognition site for a meganuclease (i.e., an endonuclease whose recognition sequence is so large that it does not occur, or occurs only rarely, in the genome of interest) into the desired genomic region.

Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, for example, United States Patent Publications 20030232410; 20050208489; 20050026157; 20050064474; and 20060188987, and International Publication WO 2007/014275, the disclosures of which are incorporated by reference in their entireties for all purposes.

However, there remain needs for compositions and methods for stable targeted integration into a safe harbor locus within the genome, in particular, the non-essential endogenous PPP1R12C (also known as p84 and/or AAVS1) gene locus.

SUMMARY

The present disclosure provides method and compositions for expressing one or more products of an exogenous nucleic acid sequence (i.e. a protein or a RNA molecule) that has been integrated into the PPP1R12C gene in a cell. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.). The exogenous nucleic acid sequence is introduced into the cell such that it is integrated into the genome of the cell in the PPP1R12C gene, which lies on chromosome 19.

Integration of the exogenous nucleic acid sequence into the PPP1R12C gene is facilitated by targeted double-strand cleavage of the genome in the PPP1R12C gene. Cleavage is targeted to the PPP1R12C gene through the use of fusion proteins comprising a zinc finger DNA binding domain, which is engineered to bind a sequence within PPP1R12C, and a cleavage domain or a cleavage half-domain. Such cleavage stimulates integration of exogenous polynucleotide sequences at or near the cleavage site. Integration of exogenous sequences can proceed through both homology-dependent and homology-independent mechanisms.

In one aspect, disclosed herein are engineered zinc finger proteins that bind to a target site in the PPP1R12C gene, for example, any of the engineered zinc finger proteins comprising the recognition helices shown in Table 1. In certain embodiments, the engineered zinc finger protein comprises four zinc fingers designated F1 to F4 from N-terminus to C-terminus and wherein F1-F4 comprise the following sequences: F1: YNWHLQR (SEQ ID NO:16); F2: RSD-HLTT (SEQ ID NO:8); F3: HNYARDC (SEQ ID NO:9); and F4: QNSTRIG (SEQ ID NO:15). In other embodiments, the engineered zinc finger protein comprises four zinc fingers designated F1 to F4 and where F1 comprises QSSN-LAR (SEQ ID NO:3); F2 comprises RTDYLVD (SEQ ID NO:11); F3 comprises YNTHLTR (SEQ ID NO:12); and F4 comprises QGYNLAG (SEQ ID NO:13). In still further embodiments, the disclosure includes engineered zinc finger proteins including 2 or 3 zinc fingers having the recognition helices of a ZFN shown in Table 1. For example, provided herein are engineered zinc finger proteins comprising four zinc fingers designated F1 to F4 from N-terminus to C-terminus, wherein the proteins comprise F1, F2 and F3; or F1, F3, F4; or F1, F2, F4; or F2, F3 and F4; or F1 and F2; or F1 and F3; or F1 and F4; or F2 and F3; or F2 and F4; or F3 and F4 of any of the ZFNs shown in Table 1 and wherein the remaining fingers comprise sequences that differ from the individual finger sequences shown in Table 1. Any of the zinc finger proteins described herein may further comprise a functional domain, for example a cleavage domain or cleavage half-domain (e.g., the cleavage half-domain is from a Type IIS restriction endonuclease such as FokI or StsI).

In another aspect, disclosed herein is a method for expressing the product of an exogenous nucleic acid sequence in a cell, the method comprising: (a) expressing a first fusion protein in the cell, the first fusion protein comprising a first zinc finger binding domain and a first cleavage half-domain, wherein the first zinc finger binding domain has been engineered to bind to a first target site in the PPP1R12C gene of the genome of the cell; (b) expressing a second fusion protein in the cell, the second fusion protein comprising a second zinc finger binding domain and a second cleavage half domain, wherein the second zinc finger binding domain binds to a second target site in the PPP1R12C gene of the genome of the cell, wherein the second target site is different from the first target site; and (c) contacting the cell with a polynucleotide comprising an exogenous nucleic acid sequence and a first nucleotide sequence that is homologous to a first sequence in the PPP1R12C gene; wherein binding of the first fusion protein to the first target site, and binding of the second fusion protein to the second target site, positions the cleavage half-domains such that the genome of the cell is cleaved in the PPP1R12C gene, thereby resulting in integration of the exogenous sequence into the genome of the cell in the PPP1R12C gene and expression of the product of the exogenous sequence.

The exogenous nucleic acid sequence may comprise a sequence encoding one or more functional polypeptides (e.g., a cDNA), with or without one or more promoters and/or may produce one or more RNA sequences (e.g., via one or more shRNA expression cassettes). In certain embodiments, the nucleic acid sequence comprises a promoterless sequence encoding an antibody, an antigen, an enzyme, a growth factor, a receptor (cell surface or nuclear), a hormone, a lymphokine, a cytokine, a reporter, functional fragments of any of the above and combinations of the above. Expression of the integrated sequence is then ensured by transcription driven by the endogenous PPP1R12C promoter. In other embodiments, a "tandem" cassette is integrated into the PPP1R12C locus in this manner, the first component of the cassette comprising a promotorless sequence as described above, followed by a transcription termination sequence, and a second sequence, encoding an autonomous expression cassette.

In certain embodiments, the polynucleotide further comprises a second nucleotide sequence that is homologous to a second sequence in the PPP1R12C gene. The second nucleotide sequence may be identical to the second sequence in the PPP1R12C gene. Furthermore, in embodiments comprising first and second nucleotide sequences, the first nucleotide sequence may be identical to the first sequence in the PPP1R12C gene and the second nucleotide sequence may be homologous but non-identical to a second sequence in the PPP1R12C gene. In any of the methods described herein, the first and second nucleotide sequences flank the exogenous sequence.

In certain embodiments, the polynucleotide is a plasmid. In other embodiments, the polynucleotide is a linear DNA molecule.

In another aspect, provided herein is a method for integrating an exogenous sequence into the PPP1R12C gene in the genome of a cell, the method comprising: (a) expressing a first fusion protein in the cell, the first fusion protein comprising a first zinc finger binding domain and a first cleavage half-domain, wherein the first zinc finger binding domain has been engineered to bind to a first target site in the PPP1R12C locus in the genome of the cell; (b) expressing a second fusion protein in the cell, the second fusion protein comprising a second zinc finger binding domain and a second cleavage half domain, wherein the second zinc finger binding domain binds to a second target site in the PPP1R12C locus in the genome of the cell, wherein the second target site is different from the first target site; and (c) contacting the cell with a polynucleotide comprising an exogenous nucleic acid sequence; wherein binding of the first fusion protein to the first target site, and binding of the second fusion protein to the second target site, positions the cleavage half-domains such that the genome of the cell is cleaved in the PPP1R12C locus, thereby resulting in homology dependent integration of the exogenous sequence into the genome of the cell within the PPP1R12C locus. In certain embodiments, an exogenous sequence encoding a functional polypeptide is inserted into the PPP1R12C gene.

In any of the methods described herein, the first and second cleavage half-domains are from a Type IIS restriction endonuclease, for example, FokI or StsI. Furthermore, in any of the methods described herein, at least one of the fusion proteins may comprise an alteration in the amino acid sequence of the dimerization interface of the cleavage half-domain, for example such that obligate heterodimers of the cleavage half-domains are formed.

In any of the methods described herein, the cell can be a mammalian cell, for example, a human cell. Furthermore, the cell may be arrested in the G2 phase of the cell cycle. In addition, in any of the methods described herein, the first and/or second zinc finger binding domain may comprise a zinc finger protein having the recognition helices set forth in Table 1 (e.g., methods in which the pair of ZFNs used comprises ZFN 15556 and ZFN 15590).

The present subject matter thus includes, but is not limited to, the following embodiments:

1. A method for expressing the product of an exogenous nucleic acid sequence in a cell, the method comprising:

(a) expressing a first fusion protein in the cell, the first fusion protein comprising a first zinc finger binding domain and a first cleavage half-domain, wherein the first zinc finger binding domain has been engineered to bind to a first target site in the PPP1R12C gene in the genome of the cell;

(b) expressing a second fusion protein in the cell, the second fusion protein comprising a second zinc finger binding domain and a second cleavage half domain, wherein the second zinc finger binding domain binds to a second target site in the PPP1R12C gene in the genome of the cell, wherein the second target site is different from the first target site; and (c) contacting the cell with a polynucleotide comprising an exogenous nucleic acid sequence;

wherein binding of the first fusion protein to the first target site, and binding of the second fusion protein to the second target site, positions the cleavage half-domains such that the genome of the cell is cleaved in the PPP1R12C gene, thereby resulting in the homology dependent integration of the exogenous sequence into the genome of the cell in the PPP1R12C gene and expression of the product of the exogenous sequence.

2. The method according to 1, wherein the exogenous nucleic acid sequence encodes a polypeptide.

3. The method according to 2, wherein the polypeptide is selected from the group consisting of an antibody, an antigen, an enzyme, a growth factor, a receptor (cell surface or nuclear), a hormone, a lymphokine, a cytokine, a reporter, functional fragments thereof and combinations thereof 4. The method according to any of 1 to 3, wherein the exogenous sequence further comprises a promoter.

5. The method according to 4, wherein the polynucleotide further comprises a first nucleotide sequence that is homologous but non-identical to a first sequence in the PPP1R12C gene.

6. The method according to 5, wherein the polynucleotide further comprises a second nucleotide sequence that is homologous but non-identical to a second sequence in the PPP1R12C gene.

7. The method according to 6, wherein the first and second nucleotide sequences flank the exogenous sequence.

8. The method of any of any of 1 to 7, wherein the polynucleotide is a plasmid.

9. The method of 1, wherein the polynucleotide is a linear DNA molecule.

10. The method according to any of 1 to 9, wherein the first and second cleavage half-domains are from a Type IIS restriction endonuclease.

11. The method according to 10, wherein the Type IIS restriction endonuclease is selected from the group consisting of FokI and StsI.

12. The method according to any of 1 to 12, wherein the cell is arrested in the G2 phase of the cell cycle.

13. The method according to any of 1 to 11, wherein at least one of the fusion proteins comprises an alteration in the amino acid sequence of the dimerization interface of the cleavage half-domain.

14. The method according to 1 to 13, wherein the cell is a mammalian cell.

15. The method according to 14, wherein the cell is a human cell.

BRIEF DESCRIPTION OF THE DRAWINGS

FIGS. 3A through 3C depict targeted integration assays evaluating GFP ORF integration in cells transfected with the donor polynucleotide shown in FIG. 1 alone (lane labeled "donor only") or with the donor polynucleotide and PPP1R12C-targeted ZFNs (lane labeled "donor+ZFN"). FIG. 3A shows results in K562 cells; FIG. 3B shows results in 293T cells; and FIG. 3C shows results in Hep3B cells.

FIGS. 4A through 4F depict the percentage of GFP-positive cells as evaluated by FACS. FIG. 4A depicts GFP-positive cells in K562 cells transfected with the GFP-donor only. FIG. 4B depicts GFP-positive cells in K562 cells transfected with the GFP-donor and PPP1R12C-targeted ZFNs. FIG. 4C depicts GFP-positive cells in 293T cells transfected with the GFP-donor only. FIG. 4D depicts GFP-positive cells in 293T cells transfected with the GFP-donor and PPP1R12C-targeted ZFNs. FIG. 4E depicts GFP-positive cells in Hep3B cells transfected with the GFP-donor only. FIG. 4F depicts GFP-positive cells in Hep3B cells transfected with the GFP-donor and PPP1R12C-targeted ZFNs.

FIG. 7A is a schematic depicting integration and mRNA expression of the GFP ORF into the region cleaved by the ZFNs. FIG. 7B depicts insertion of the GFP ORF in the absence (lane 1) or presence of ZFNs (lane 2). The percentage of cells (9.6%) with integrated GFP ORF in the presence of ZFNs (lane 2) is indicated beneath lane 2.

FIGS. 8A through 8E depict integration of a donor containing a promoter transcription unit (PTU). FIG. 8A shows the epigenetic stability of GFP expression in K562 cells when driven by the endogenous p84 promoter. The mean fluorescence intensity (MFI) of a GFP-positive cell pool (crosses), a clone derived by limiting dilution that is homozygous at p84 for the GFP ORF (squares) and heterozygous for it (triangles), measured over 25 days—ca. 30 cell doublings—of growth in nonselective medium is shown. Untransformed K562 are also shown (diamonds). FIG. 8B depicts a graphical schematic of tandem "marker-PTU" addition process showing the integration of a shRNA expression cassette in addition to the GFP ORF screening marker. FIG. 8C depicts efficient long-term function of a PTU transferred to the p84 locus using ZFNs. Cells were (in order of appearance in the figure) left untreated, transiently transfected with an shRNA-encoding plasmid against CD58, or transfected with ZFNs and a donor plasmid schematically depicted in FIG. 8C. CD58 expression on the cell surface was assayed by immunofluorescence and FACS using an anti-CD58 antibody. FIG. 8D depicts the FACS staining profile of cells double-transgenic at p84. FIG. 8E depicts the results of quantitative PCR-based assay on GFP-positive cells carrying solely the GFP ORF (middle lane) or the GFP ORF in tandem with a PTU encoding an shRNA against CD58 (right lane). Numbers represent the percent of the population that has been modified.

FIG. 9A is a reproduction of a gel showing comparison of genome editing efficiency driven by IL2Rγ-targeting and p84-targeting ZFNs at their intended loci. K562 cells were transfected with the indicated reagents. Gene disruption frequency at the target loci was assayed by Surveyor™ endonuclease as described in Miller et al. (2007) *Nat. Biotechnol.* 25(7):778-785 and is indicated below the appropriate lanes. FIG. 9B is a graph depicting overall nucleus-wide levels of H2A.X staining in cells treated as indicated, using a FACS based assay as described in Miller et al. (2007) *Nat. Biotechnol.* 25(7):778-785.

DETAILED DESCRIPTION

Figure 1:
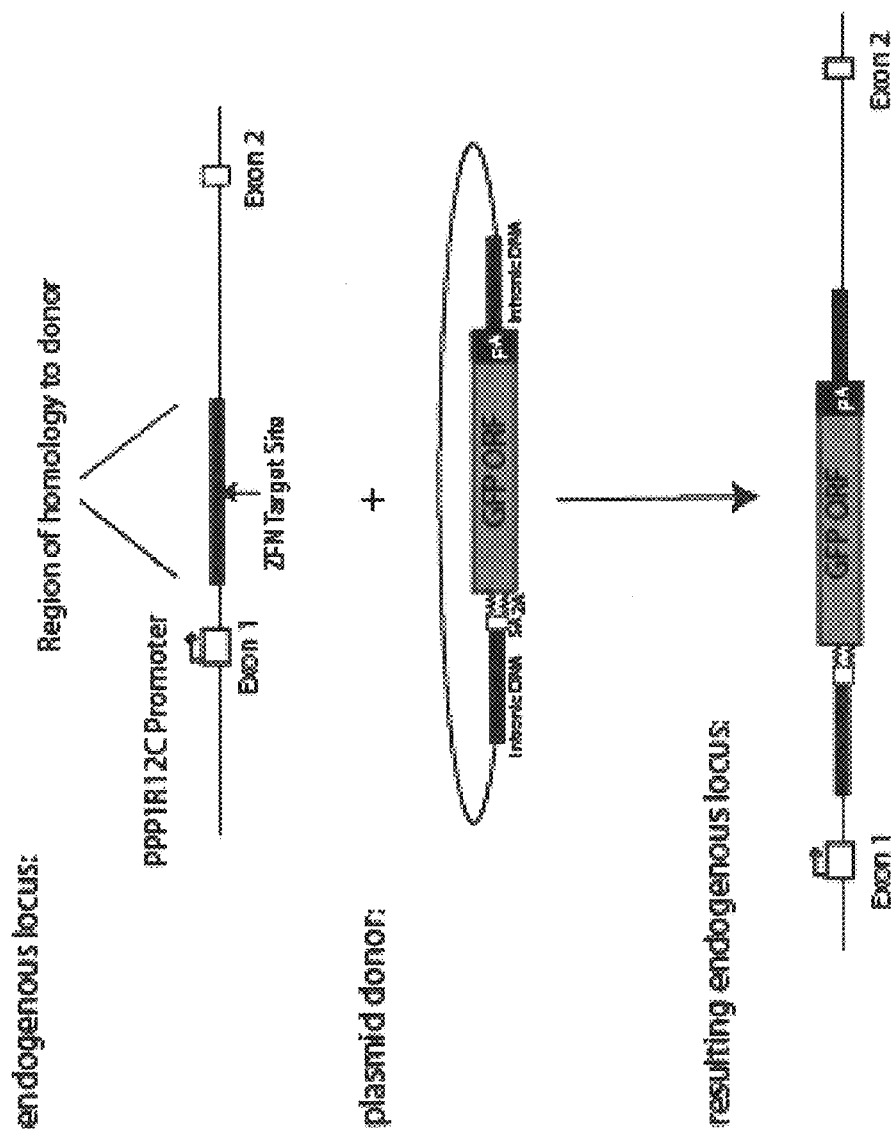
FIG. 1 is a schematic depicting various polynucleotide components involved in zinc finger nuclease (ZFN)-driven targeted insertion into the PPP1R12C gene. See, Example 1. The top line depicts the endogenous PPP1R12C locus, including an exemplary ZFN target site and region of homology to an exemplary plasmid donor encoding GFP. The middle line depicts a circular GFP plasmid donor. In the presence of the ZFN, the GFP coding sequence carried on the plasmid donor is inserted into the PPP1R12C gene as shown in the bottom schematic. The embodiment displayed in the figure allows for the transcription of the integrated GFP open reading frame and its subsequent translation by the integration of a splice acceptor (SA) site, followed by a translation interruption-reinitiation signal (2A; Fang et al (2005) *Nat Biotech.* 23:584), followed by the GFP open reading frame, and a polyadenylation signal.
Figure 2:
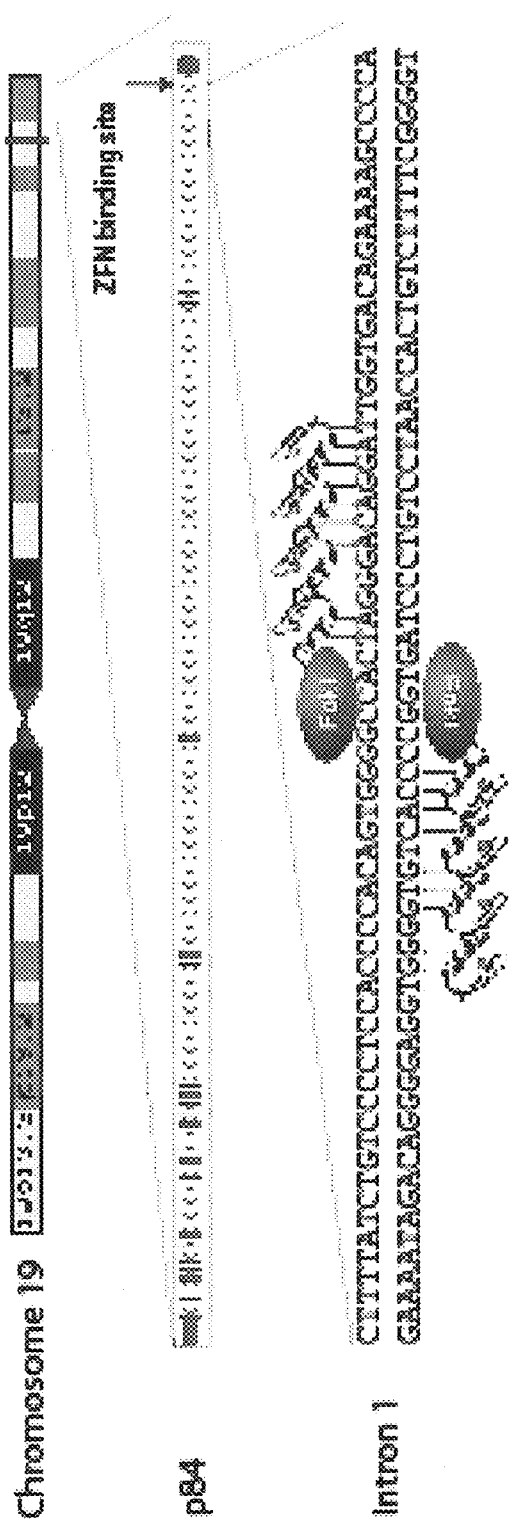
FIG. 2 schematically depicts chromosome 19 (top line) and the locations of PPP1R12C/p84 within chromosome 19 (middle line). An exemplary ZFN binding site is shown on the bottom line in intron 1 of PPP1R12C.

The present disclosure relates to methods and composition for targeted integration (TI) into the human PPP1R12C gene, which lies on chromosome 19. PPP1R12C is the major site of integration into the human genome of adeno-associated virus and no pathophysiological event has ever been associated with AAV infection (Warrington & Herzog (2006) *Hum Genet* 119:571-603), indicating that the loss of PPP1R12C function is tolerated by human cells and that this locus can be considered a "safe harbor" for targeted integration. Moreover, the PPP1R12C gene is broadly transcribed. Thus, the inserted (donor) sequence can be promoterless and transcription of the integrated open reading frame can occur from the endogenous gene promoter, which lowers the likelihood of a severe adverse event due to random integration of the donor and/or the spurious activation of an endogenous gene by the promoter carried on the donor (see, e.g., Kohn et al. *Nat Rev Cancer* 3:477-488)

Compositions useful for targeted cleavage and recombination into the PPP1R12C gene include fusion proteins comprising a cleavage domain (or a cleavage half-domain) and a zinc finger binding domain, polynucleotides encoding these proteins and combinations of polypeptides and polypeptide-encoding polynucleotides. A zinc finger binding domain can comprise one or more zinc fingers (e.g., 2, 3, 4, 5, 6, 7, 8, 9 or more zinc fingers), and can be engineered to bind to any sequence within PPP1R12C. The presence of such a fusion protein (or proteins) in a cell will result in binding of the fusion protein(s) to its (their) binding site(s) and cleavage within the endogenous PPP1R12C gene.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+Swiss protein+Spupdate+PIR. Details of these programs can be found on the internet. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage domain" comprises one or more polypeptide sequences which possesses catalytic activity for DNA cleavage. A cleavage domain can be contained in a single polypeptide chain or cleavage activity can result from the association of two (or more) polypeptides.

A "cleavage half-domain" is a polypeptide sequence which, in conjunction with a second polypeptide (either identical or different) forms a complex having cleavage activity (preferably double-strand cleavage activity).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a coding sequence for any polypeptide or fragment thereof, a functioning version of a malfunctioning endogenous molecule or a malfunctioning version of a normally-functioning endogenous molecule. Additionally, an exogenous molecule can comprise a coding sequence from another species that is an ortholog of an endogenous gene in the host cell.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

"Eukaryotic" cells include, but are not limited to, fungal cells (such as yeast), plant cells, animal cells, mammalian cells and human cells.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

Target Sites

The disclosed methods and compositions include fusion proteins comprising a cleavage domain (or a cleavage half-domain) and a zinc finger domain, in which the zinc finger domain, by binding to a sequence in the human PPP1R12C locus directs the activity of the cleavage domain (or cleavage half-domain) to the vicinity of the sequence and, hence, induces cleavage (e.g., a double stranded break) in PPP1R12C. As set forth elsewhere in this disclosure, a zinc finger domain can be engineered to bind to virtually any desired sequence. Accordingly, one or more zinc finger binding domains can be engineered to bind to one or more sequences in the PPP1R12C gene. Expression of a fusion protein comprising a zinc finger binding domain and a cleavage domain (or of two fusion proteins, each comprising a zinc finger binding domain and a cleavage half-domain), in a cell, effects cleavage in the PPP1R12C gene.

Selection of a sequence in PPP1R12C for binding by a zinc finger domain (e.g., a target site) can be accomplished, for example, according to the methods disclosed in co-owned U.S. Pat. No. 6,453,242 (Sep. 17, 2002), which also discloses methods for designing ZFPs to bind to a selected sequence. It will be clear to those skilled in the art that simple visual inspection of a nucleotide sequence can also be used for selection of a target site. Accordingly, any means for target site selection can be used in the methods described herein.

Target sites are generally composed of a plurality of adjacent target subsites. A target subsite refers to the sequence (usually either a nucleotide triplet, or a nucleotide quadruplet that can overlap by one nucleotide with an adjacent quadruplet) bound by an individual zinc finger. See, for example, WO 02/077227. If the strand with which a zinc finger protein makes most contacts is designated the target strand "primary recognition strand," or "primary contact strand," some zinc finger proteins bind to a three base triplet in the target strand and a fourth base on the non-target strand. A target site generally has a length of at least 9 nucleotides and, accordingly, is bound by a zinc finger binding domain comprising at least three zinc fingers. However binding of, for example, a 4-finger binding domain to a 12-nucleotide target site, a 5-finger binding domain to a 15-nucleotide target site or a 6-finger binding domain to an 18-nucleotide target site, is also possible. As will be apparent, binding of larger binding domains (e.g., 7-, 8-, 9-finger and more) to longer target sites is also possible.

It is not necessary for a target site to be a multiple of three nucleotides. For example, in cases in which cross-strand interactions occur (see, e.g., U.S. Pat. No. 6,453,242 and WO 02/077227), one or more of the individual zinc fingers of a multi-finger binding domain can bind to overlapping quadruplet subsites. As a result, a three-finger protein can bind a 10-nucleotide sequence, wherein the tenth nucleotide is part of a quadruplet bound by a terminal finger, a four-finger protein can bind a 13-nucleotide sequence, wherein the thirteenth nucleotide is part of a quadruplet bound by a terminal finger, etc.

The length and nature of amino acid linker sequences between individual zinc fingers in a multi-finger binding domain also affects binding to a target sequence. For example, the presence of a so-called "non-canonical linker," "long linker" or "structured linker" between adjacent zinc fingers in a multi-finger binding domain can allow those fingers to bind subsites which are not immediately adjacent. Non-limiting examples of such linkers are described, for example, in U.S. Pat. No. 6,479,626 and WO 01/53480. Accordingly, one or more subsites, in a target site for a zinc finger binding domain, can be separated from each other by 1, 2, 3, 4, 5 or more nucleotides. To provide but one example, a four-finger binding domain can bind to a 13-nucleotide target site comprising, in sequence, two contiguous 3-nucleotide subsites, an intervening nucleotide, and two contiguous triplet subsites.

Distance between sequences (e.g., target sites) refers to the number of nucleotides or nucleotide pairs intervening between two sequences, as measured from the edges of the sequences nearest each other.

In certain embodiments in which cleavage depends on the binding of two zinc finger domain/cleavage half-domain fusion molecules to separate target sites, the two target sites can be on opposite DNA strands (Example 1). In other embodiments, both target sites are on the same DNA strand.

DNA-Binding Domains

Any DNA-binding domain can be used in the methods disclosed herein. In certain embodiments, the DNA binding domain comprises a zinc finger protein. A zinc finger binding domain comprises one or more zinc fingers. Miller et al. (1985) *EMBO J.* 4:1609-1614; Rhodes (1993) *Scientific American* February: 56-65; U.S. Pat. No. 6,453,242. The zinc finger binding domains described herein generally include 2, 3, 4, 5, 6 or even more zinc fingers.

Typically, a single zinc finger domain is about 30 amino acids in length. Structural studies have demonstrated that each zinc finger domain (motif) contains two beta sheets (held in a beta turn which contains the two invariant cysteine residues) and an alpha helix (containing the two invariant histidine residues), which are held in a particular conformation through coordination of a zinc atom by the two cysteines and the two histidines.

Zinc fingers include both canonical $C_2H_2$ zinc fingers (i.e., those in which the zinc ion is coordinated by two cysteine and two histidine residues) and non-canonical zinc fingers such as, for example, $C_3H$ zinc fingers (those in which the zinc ion is coordinated by three cysteine residues and one histidine residue) and $C_4$ zinc fingers (those in which the zinc ion is coordinated by four cysteine residues). See also WO 02/057293.

Zinc finger binding domains can be engineered to bind to a target site (see above) in PPP1R12C using standard techniques. See, Example 1; co-owned U.S. Pat. Nos. 6,453,242 and 6,534,261, including references cited therein. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Enhancement of binding specificity for zinc finger binding domains has been described, for example, in co-owned WO 02/077227.

Since an individual zinc finger binds to a three-nucleotide (i.e., triplet) sequence (or a four-nucleotide sequence which can overlap, by one nucleotide, with the four-nucleotide binding site of an adjacent zinc finger), the length of a sequence to which a zinc finger binding domain is engineered to bind (e.g., a target sequence) will determine the number of zinc fingers in an engineered zinc finger binding domain. For example, for ZFPs in which the finger motifs do not bind to overlapping subsites, a six-nucleotide target sequence is bound by a two-finger binding domain; a nine-nucleotide target sequence is bound by a three-finger binding domain, etc. As noted herein, binding sites for individual zinc fingers (i.e., subsites) in a target site need not be contiguous, but can be separated by one or several nucleotides, depending on the length and nature of the amino acids sequences between the zinc fingers (i.e., the inter-finger linkers) in a multi-finger binding domain.

In a multi-finger zinc finger binding domain, adjacent zinc fingers can be separated by amino acid linker sequences of approximately 5 amino acids (so-called "canonical" inter-finger linkers) or, alternatively, by one or more non-canonical linkers. See, e.g., co-owned U.S. Pat. Nos. 6,453,242 and 6,534,261. For engineered zinc finger binding domains comprising more than three fingers, insertion of longer ("non-canonical") inter-finger linkers between certain of the zinc fingers may be preferred as it may increase the affinity and/or specificity of binding by the binding domain. See, for example, U.S. Pat. No. 6,479,626 and WO 01/53480. Accordingly, multi-finger zinc finger binding domains can also be characterized with respect to the presence and location of non-canonical inter-finger linkers. For example, a six-finger zinc finger binding domain comprising three fingers (joined by two canonical inter-finger linkers), a long linker and three additional fingers (joined by two canonical inter-finger linkers) is denoted a 2×3 configuration. Similarly, a binding domain comprising two fingers (with a canonical linker therebetween), a long linker and two additional fingers (joined by a canonical linker) is denoted a 2×2 protein. A protein comprising three two-finger units (in each of which the two fingers are joined by a canonical linker), and in which each two-finger unit is joined to the adjacent two finger unit by a long linker, is referred to as a 3×2 protein.

The presence of a long or non-canonical inter-finger linker between two adjacent zinc fingers in a multi-finger binding domain often allows the two fingers to bind to subsites which are not immediately contiguous in the target sequence. Accordingly, there can be gaps of one or more nucleotides between subsites in a target site; i.e., a target site can contain one or more nucleotides that are not contacted by a zinc finger. For example, a 2×2 zinc finger binding domain can bind to two six-nucleotide sequences separated by one nucleotide, i.e., it binds to a 13-nucleotide target site. See also Moore et al. (2001a) Proc. Natl. Acad. Sci. USA 98:1432-1436; Moore et al. (2001b) Proc. Natl. Acad. Sci. USA 98:1437-1441 and WO 01/53480.

As mentioned previously, a target subsite is a three- or four-nucleotide sequence that is bound by a single zinc finger. For certain purposes, a two-finger unit is denoted a binding module. A binding module can be obtained by, for example, selecting for two adjacent fingers in the context of a multi-finger protein (generally three fingers) which bind a particular six-nucleotide target sequence. Alternatively, modules can be constructed by assembly of individual zinc fingers. See also WO 98/53057 and WO 01/53480.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128.

Cleavage Domains

The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). Non limiting examples of homing endonucleases and meganucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. One or more of these enzymes (or functional fragments thereof) can be used as a source of cleavage domains and cleavage half-domains.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in co-owned International Publication WO 2007/014275, incorporated by reference herein in its entirety.

To enhance cleavage specificity, cleavage domains may also be modified. In certain embodiments, variants of the cleavage half-domain are employed, which variants that minimize or prevent homodimerization of the cleavage half-domains. Non-limiting examples of such modified cleavage half-domains are described in detail in WO 2007/014275, incorporated by reference in its entirety herein. See, also, Examples. In certain embodiments, the cleavage domain comprises an engineered cleavage half-domain (also referred to as dimerization domain mutants) that minimize or prevent homodimerization are known to those of skill the art and described for example in U.S. Patent Publication Nos. 20050064474 and 20060188987, incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains. See, e.g., U.S. Patent Publication Nos. 20050064474 and 20060188987; International Patent Publication WO 07/139898; Miller et al. (2007) *Nat. Biotechnol.* 25(7):778-785.

Additional engineered cleavage half-domains of Fok I form an obligate heterodimers can also be used in the ZFNs described herein. The first cleavage half-domain includes mutations at amino acid residues at positions 490 and 538 of Fok I and the second cleavage half-domain includes mutations at amino acid residues 486 and 499.

In certain embodiments, the cleavage domain comprises two cleavage half-domains, both of which are part of a single polypeptide comprising a binding domain, a first cleavage half-domain and a second cleavage half-domain. The cleavage half-domains can have the same amino acid sequence or different amino acid sequences, so long as they function to cleave the DNA.

In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotides or more). In general, the point of cleavage lies between the target sites.

Zinc Finger Domain-Cleavage Domain Fusions

Methods for design and construction of fusion proteins (and polynucleotides encoding same) are known to those of skill in the art. For example, methods for the design and construction of fusion protein comprising zinc finger proteins (and polynucleotides encoding same) are described in co-owned U.S. Pat. Nos. 6,453,242 and 6,534,261; and International Publication WO 2007/014275. In certain embodiments, polynucleotides encoding such fusion proteins are constructed. These polynucleotides can be inserted into a vector and the vector can be introduced into a cell (see below for additional disclosure regarding vectors and methods for introducing polynucleotides into cells).

In certain embodiments of the methods described herein, a fusion protein comprises a zinc finger binding domain and a cleavage half-domain from the Fok I restriction enzyme, and two such fusion proteins are expressed in a cell. Expression of two fusion proteins in a cell can result from delivery of the two proteins to the cell; delivery of one protein and one nucleic acid encoding one of the proteins to the cell; delivery of two nucleic acids, each encoding one of the proteins, to the cell; or by delivery of a single nucleic acid, encoding both proteins, to the cell. In additional embodiments, a fusion protein comprises a single polypeptide chain comprising two cleavage half domains and a zinc finger binding domain. In this case, a single fusion protein is expressed in a cell and, without wishing to be bound by theory, is believed to cleave DNA as a result of formation of an intramolecular dimer of the cleavage half-domains.

Two fusion proteins, each comprising a zinc finger binding domain and a cleavage half-domain, may be expressed in a cell, and bind to target sites which are juxtaposed in such a way that a functional cleavage domain is reconstituted and DNA is cleaved in the vicinity of the target sites. In one embodiment, cleavage occurs between the target sites of the two zinc finger binding domains. One or both of the zinc finger binding domains and/or cleavage domains can be engineered. See, Example 1.

The components of the fusion proteins (e.g., ZFP-Fok I fusions) may be arranged such that the zinc finger domain is nearest the amino terminus of the fusion protein, and the cleavage half-domain is nearest the carboxy-terminus. Dimerization of the cleavage half-domains to form a functional nuclease is brought about by binding of the fusion proteins to sites on opposite DNA strands, with the 5' ends of the binding sites being proximal to each other.

Alternatively, the components of the fusion proteins (e.g., ZFP-Fok I fusions) may be arranged such that the cleavage half-domain is nearest the amino terminus of the fusion protein, and the zinc finger domain is nearest the carboxy-terminus. In these embodiments, dimerization of the cleavage half-domains to form a functional nuclease is brought about by binding of the fusion proteins to sites on opposite DNA strands, with the 3' ends of the binding sites being proximal to each other.

In yet additional embodiments, a first fusion protein contains the cleavage half-domain nearest the amino terminus of the fusion protein, and the zinc finger domain nearest the carboxy-terminus, and a second fusion protein is arranged such that the zinc finger domain is nearest the amino terminus of the fusion protein, and the cleavage half-domain is nearest the carboxy-terminus. In these embodiments, both fusion proteins bind to the same DNA strand, with the binding site of the first fusion protein containing the zinc finger domain nearest the carboxy terminus located to the 5' side of the binding site of the second fusion protein containing the zinc finger domain nearest the amino terminus.

The two fusion proteins can bind in the region of interest in the same or opposite polarity, and their binding sites (i.e., target sites) can be separated by any number of nucleotides, e.g., from 0 to 200 nucleotides or any integral value therebetween. In certain embodiments, the binding sites for two fusion proteins, each comprising a zinc finger binding domain and a cleavage half-domain, can be located between 5 and 18 nucleotides apart, for example, 5-8 nucleotides apart, or 15-18 nucleotides apart, or 6 nucleotides apart, or 16 nucleotides apart, as measured from the edge of each binding site nearest the other binding site, and cleavage occurs between the binding sites.

The site at which the DNA is cleaved generally lies between the binding sites for the two fusion proteins. Double-strand breakage of DNA often results from two single-strand breaks, or "nicks," offset by 1, 2, 3, 4, 5, 6 or more nucleotides, (for example, cleavage of double-stranded DNA by native Fok I results from single-strand breaks offset by 4 nucleotides). Thus, cleavage does not necessarily occur at exactly opposite sites on each DNA strand. In addition, the structure of the fusion proteins and the distance between the target sites can influence whether cleavage occurs adjacent a single nucleotide pair, or whether cleavage occurs at several sites. However, for targeted integration, cleavage within a range of nucleotides is generally sufficient, and cleavage between particular base pairs is not required.

In the disclosed fusion proteins, the amino acid sequence between the zinc finger domain and the cleavage domain (or cleavage half-domain) is denoted the "ZC linker." The ZC linker is to be distinguished from the inter-finger linkers discussed above. ZC linkers are described in detail, for example, in WO 2007/014275.

As discussed in detail below, the fusion protein (ZFN), or a polynucleotide encoding same, is introduced into a cell. Once introduced into, or expressed in, the cell, the fusion protein binds to the target sequence in PPP1R12C and cleaves within this gene locus.

Targeted Integration into the PPP1R12C Gene

The disclosed methods and compositions can be used to cleave DNA in the PPP1R12C gene of cellular chromatin, which facilitates the stable, targeted integration of an exogenous sequence into the "safe harbor" of the PPP1R12C locus. As noted above, loss of function of endogenous PPP1R12C is well tolerated by human cells and sequences integrated within this gene are broadly transcribed from the endogenous promoter. Accordingly, PPP1R12C is a desirable site for targeted integration of exogenous sequences.

For targeted integration into PPP1R12C, one or more zinc finger binding domains are engineered to bind a target site at or near the predetermined cleavage site, and a fusion protein comprising the engineered zinc finger binding domain and a cleavage domain is expressed in a cell. Upon binding of the zinc finger portion of the fusion protein to the target site, the DNA is cleaved, preferably via a double stranded break, near the target site by the cleavage domain.

The presence of a double-stranded break in the PPP1R12C locus facilitates integration of exogenous sequences via homologous recombination. Thus, the polynucleotide comprising the exogenous sequence to be inserted into the PPP1R12C gene will include one or more regions of homology with PPP1R12C gene to facilitate homologous recombination.

Any sequence of interest (exogenous sequence) can be introduced into the PPP1R12C locus as described herein. Exemplary exogenous sequences include, but are not limited to any polypeptide coding sequence (e.g., cDNAs), promoter, enhancer and other regulatory sequences, shRNA expression cassettes, epitope tags, marker genes, cleavage enzyme recognition sites and various types of expression constructs. Such sequences can be readily obtained using standard molecular biological techniques (cloning, synthesis, etc.) and/or are commercially available. For example, MISSION™ TRC shRNA libraries are commercially available from Sigma.

Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), cell surface antigens (e.g., ΔNGFR) and proteins which mediate enhanced cell growth and/or gene amplification (e.g., dihydrofolate reductase). Epitope tags include, for example, one or more copies of FLAG, His, myc, Tap, HA or any detectable amino acid sequence.

In a preferred embodiment, the exogenous sequence comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs. The exogenous sequence may also encode transcriptional regulatory factors.

For example, the exogenous sequence targeted to the PPP1R12C locus comprises a sequence encoding a polypeptide that is lacking or non-functional in the subject having a genetic disease, including but not limited to any of the following genetic diseases: achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, *porphyria*, Prader-Willi syndrome, progeria, *Proteus* syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted integration include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

In certain embodiments, the exogenous sequences can comprise a marker gene (described above), allowing selection of cells that have undergone targeted integration, and a linked sequence encoding an additional functionality.

Furthermore, although not required for expression, exogenous sequences may also be transcriptional or translational regulatory sequences, for example, promoters, enhancers, insulators, internal ribosome entry sites, sequences encoding 2A peptides and/or polyadenylation signals.

Targeted integration of exogenous sequences, as disclosed herein, can be used to generate cells and cell lines for protein expression. See, for example, co-owned U.S. Patent Application Publication No. 2006/0063231 (the disclosure of which is hereby incorporated by reference herein, in its entirety, for all purposes). For optimal expression of one or more proteins encoded by exogenous sequences integrated into a genome, the chromosomal integration site should be compatible with high-level transcription of the integrated sequences, preferably in a wide range of cell types and developmental states. However, it has been observed that transcription of integrated sequences varies depending on the integration site due to, among other things, the chromatin structure of the genome at the integration site. Accordingly, genomic target sites that support high-level transcription of integrated sequences are desirable. In certain embodiments, it will also be desirable that integration of exogenous sequences not result in ectopic activation of one or more cellular genes (e.g., oncogenes). On the other hand, in the case of integration of promoter and/or enhancer sequences, ectopic expression may be desired.

The exogenous (donor) sequence can be introduced into the cell prior to, concurrently with, or subsequent to, expression of the fusion protein(s). The donor polynucleotide contains sufficient homology to a genomic sequence to support homologous recombination (or homology-directed repair) between it and the genomic sequence to which it bears homology. Approximately 25, 50, 100, 200, 500, 750, 1,000, 1,500, 2,000 nucleotides or more of sequence homology between a donor and a genomic sequence (or any integral value between 10 and 2,000 nucleotides, or more) will support homologous recombination therebetween. Donor sequences can range in length from 10 to 5,000 nucleotides (or any integral value of nucleotides therebetween) or longer. It will be readily apparent that the donor sequence is typically not identical to the genomic sequence that it replaces. For example, the sequence of the donor polynucleotide can contain one or more single base changes, insertions, deletions, inversions or rearrangements with respect to the genomic sequence, so long as sufficient homology with chromosomal sequences is present.

Alternatively, a donor sequence can contain a non-homologous sequence flanked by two regions of homology. Additionally, donor sequences can comprise a vector molecule containing sequences that are not homologous to the region of interest in cellular chromatin. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

A donor molecule can contain several, discontinuous regions of homology to cellular chromatin. For example, for regions of homology can flank two or more regions containing the desired alterations.

The donor polynucleotide can be DNA or RNA, single-stranded or double-stranded and can be introduced into a cell in linear or circular form. If introduced in linear form, the ends of the donor sequence can be protected (e.g., from exonucleolytic degradation) by methods known to those of skill in the art. See, WO 2007/014275. A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus).

Methods and compositions are also provided that may enhance levels of targeted recombination including, but not limited to, the use of additional ZFP-functional domain fusions. See, WO 2007/014275.

Further increases in efficiency of targeted recombination, in cells comprising a zinc finger/nuclease fusion molecule and a donor DNA molecule, are achieved by blocking the cells in the $G_2$ phase of the cell cycle, when homology-driven repair processes are maximally active. Such arrest can be achieved in a number of ways. For example, cells can be treated with e.g., drugs, compounds and/or small molecules which influence cell-cycle progression so as to arrest cells in $G_2$ phase. Exemplary molecules of this type include, but are not limited to, compounds which affect microtubule polymerization (e.g., vinblastine, nocodazole, Taxol), compounds that interact with DNA (e.g., cis-platinum(II) diamine dichloride, Cisplatin, doxorubicin) and/or compounds that affect DNA synthesis (e.g., thymidine, hydroxyurea, L-mimosine, etoposide, 5-fluorouracil). Additional increases in recombination efficiency are achieved by the use of histone deacetylase (HDAC) inhibitors (e.g., sodium butyrate, trichostatin A) which alter chromatin structure to make genomic DNA more accessible to the cellular recombination machinery.

Additional methods for cell-cycle arrest include overexpression of proteins which inhibit the activity of the CDK cell-cycle kinases, for example, by introducing a cDNA encoding the protein into the cell or by introducing into the cell an engineered ZFP which activates expression of the gene encoding the protein. Cell-cycle arrest is also achieved by inhibiting the activity of cyclins and CDKs, for example, using RNAi methods (e.g., U.S. Pat. No. 6,506,559) or by introducing into the cell an engineered ZFP which represses expression of one or more genes involved in cell-cycle progression such as, for example, cyclin and/or CDK genes. See, e.g., co-owned U.S. Pat. No. 6,534,261 for methods for the synthesis of engineered zinc finger proteins for regulation of gene expression.

Alternatively, in certain cases, targeted cleavage is conducted in the absence of a donor polynucleotide (preferably in S or $G_2$ phase), and recombination occurs between homologous chromosomes.

Delivery

The fusion protein(s) (ZFNs) can be introduced as polypeptides and/or polynucleotides. For example, two polynucleotides, each comprising sequences encoding one of the aforementioned polypeptides, can be introduced into a cell, and when the polypeptides are expressed and each binds to its target sequence, cleavage occurs at or near the target sequence. Alternatively, a single polynucleotide comprising sequences encoding both fusion polypeptides is introduced into a cell. Polynucleotides can be DNA, RNA or any modified forms or analogues or DNA and/or RNA.

The nucleic acids as described herein (e.g., a polynucleotide encoding ZFN and/or the exogenous "donor" sequence) may be introduced into a cell using any suitable method.

In certain embodiments, one or more ZFPs or ZFP fusion proteins can be cloned into a vector for transformation into prokaryotic or eukaryotic cells for replication and/or expression. Vectors can be prokaryotic vectors, e.g., plasmids, or shuttle vectors, insect vectors, or eukaryotic vectors. A nucleic acid encoding sequences described herein (ZFNs) can also be cloned into an expression vector, for administration to a plant cell, animal cell, preferably a mammalian cell or a human cell, fungal cell, bacterial cell, or protozoal cell using standard techniques described for example in Sambrook et al., supra and United States Patent Publications 20030232410; 20050208489; 20050026157; 20050064474; and 20060188987, and International Publication WO 2007/014275.

In certain embodiments, the ZFNs and donor sequences are delivered in vivo or ex vivo for gene therapy uses. Non-viral vector delivery systems for delivering polynucleotides to cells include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids in vivo or ex vivo include electroporation, lipofection (see, U.S. Pat. Nos. 5,049,386; 4,946,787 and commercially available reagents such as Transfectam™ and Lipofectin™), microinjection, biolistics, virosomes, liposomes (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787), immunoliposomes, polycation or lipid:nucleic acid conjugates, naked DNA, artificial virions, viral vector systems (e.g., retroviral, lentivirus, adenoviral, adeno-associated, vaccinia and herpes simplex virus vectors as described in WO 2007/014275 for delivering proteins comprising ZFPs) and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.) and BTX Molecular Delivery Systems (Holliston, Mass.).

In certain embodiments, for example, in which transient expression of a ZFP fusion protein is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated virus subtypes. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). In addition, self complementary recombinant adeno-associated virus (scAAV)-derived vectors can be used.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the polynucleotides (e.g., ZFN-encoding sequence and/or donor sequences) be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA) and exogenous sequence, and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Tad (differentiated antigen presenting cells) (see Inaba et al., *J. Exp. Med.* 176:1693-1702 (1992)).

Vectors (e.g., retroviruses, adenoviruses, liposomes, etc.) comprising nucleic acids as described herein can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

As noted above, one or more of the ZFN fusion proteins can be also be introduced into the cell as polypeptides using methods described for example in WO 2007/014275. Non-limiting examples of protein delivery vehicles include, "membrane translocation polypeptides," for example peptide have amphiphilic or hydrophobic amino acid subsequences that have the ability to act as membrane-translocating carriers, toxin molecules, liposomes and liposome derivatives such as immunoliposomes (including targeted liposomes).

ZFPs and expression vectors encoding ZFPs can be administered directly to the patient for targeted cleavage integration into PPP1R12C for therapeutic or prophylactic applications, for example, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, and the like.

Administration of therapeutically effective amounts is by any of the routes normally used for introducing ZFP into ultimate contact with the tissue to be treated. The ZFPs are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions that are available (see, e.g., *Remington's Pharmaceutical Sciences*, 17th ed. 1985)).

The ZFPs, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

EXAMPLES

Example 1: Design of Zinc Finger Nucleases Targeted to PPP1R12C

Fusion proteins comprising a pair of 4-fingered zinc finger protein nucleases (ZFNs) were designed as described in International Publication WO 2007/014275 and optimized optimized using phage display according to published protocols (Rebar & Pabo (1994) *Science* 263(5147):671-3; Greisman & Pabo (1997) *Science* 275(5300):657-61) to induce a double stranded break into intron 1 of PPP1R12C as shown in FIG. 1. The ZFN target sequence corresponds to positions 60318932-60318961 of the "-" strand of human chromosome 19 (UCSC human genome release March 2006).

Table 1 shows exemplary PPP1R12C-targeted ZFNs were that used for targeted integration experiments into the PPP1R12C locus.

TABLE 1

| ZFN name | Target Site | F1 | F2 | F3 | F4 |
|---|---|---|---|---|---|
| 9931 | acTAGGGACAGGATg (SEQ ID NO: 1) | QSSNLAR (SEQ ID NO: 3) | RPDFLNQ (SEQ ID NO: 4) | QSGHLAR (SEQ ID NO: 5) | RSDNLTT (SEQ ID NO: 6) |
| 10099 | ccCCACTGTGGGGTgg (SEQ ID NO: 2) | QSSHLTR (SEQ ID NO: 7) | RSDHLTT (SEQ ID NO: 8) | HNYARDC (SEQ ID NO: 9) | QKATRTT (SEQ ID NO: 10) |
| 15587 | acTAGGGACAGGATg (SEQ ID NO: 1) | QSSNLAR (SEQ ID NO: 3) | RTDYLVD (SEQ ID NO: 11) | YNTHLTR (SEQ ID NO: 12) | RSDNLTT (SEQ ID NO: 6) |
| 15590 | acTAGGGACAGGATg (SEQ ID NO: 1) | QSSNLAR (SEQ ID NO: 3) | RTDYLVD (SEQ ID NO: 11) | YNTHLTR (SEQ ID NO: 12) | QGYNLAG (SEQ ID NO: 13) |
| 15554 | ccCCACTGTGGGGTgg (SEQ ID NO: 2) | ERHHLMR (SEQ ID NO: 14) | RSDHLTT (SEQ ID NO: 8) | HNYARDC (SEQ ID NO: 9) | QNSTRIG (SEQ ID NO: 15) |

TABLE 1-continued

| ZFN name | Target Site | F1 | F2 | F3 | F4 |
|---|---|---|---|---|---|
| 15556 | ccCCACTGTGGGGTgg (SEQ ID NO: 2) | YNWHLQR (SEQ ID NO: 16) | RSDHLTT (SEQ ID NO: 8) | HNYARDC (SEQ ID NO: 9) | QNSTRIG (SEQ ID NO: 15) |
| 15557 | ccCCACTGTGGGGTgg (SEQ ID NO: 2) | LHHQLVR (SEQ ID NO: 17) | RSDHLTT (SEQ ID NO: 8) | HNYARDC (SEQ ID NO: 9) | QNSTRIG (SEQ ID NO: 15) |

Example 2: Targeted Integration into PPP1R12C Locus

A donor was designed by using a 1,647 bp fragment of the same locus (positions 60318104-60319750), and introducing a "splice acceptor—FMDV 2A—GFP—poly(A)" cassette into the position between the ZFN 9931 AND 10099 binding sites. The ZFN and donor constructs were prepared as described in Urnov et al. (2005) Nature 435:646-651 and Moehle et al (2007) PNAS 194: 305, except that obligate heterodimer forms of the FokI endonuclease were used in the ZFN expression constructs (see, Section entitled "Cleavage Domains" above) and introduced into K562, 293T, Hep3B or HEK293 cells.

Seventy two hours after transfection, the rate of targeted integration (TI) was assayed by a radiolabelled PCR assay, as described Moehle et al. (2007) Proc. Nat'l Acad. Sci. USA 104:3055-3060. Two weeks after transfection, the percentage of GFP-positive cells was assayed by FACS, also as described Moehle et al. (2007).

Figure 7:
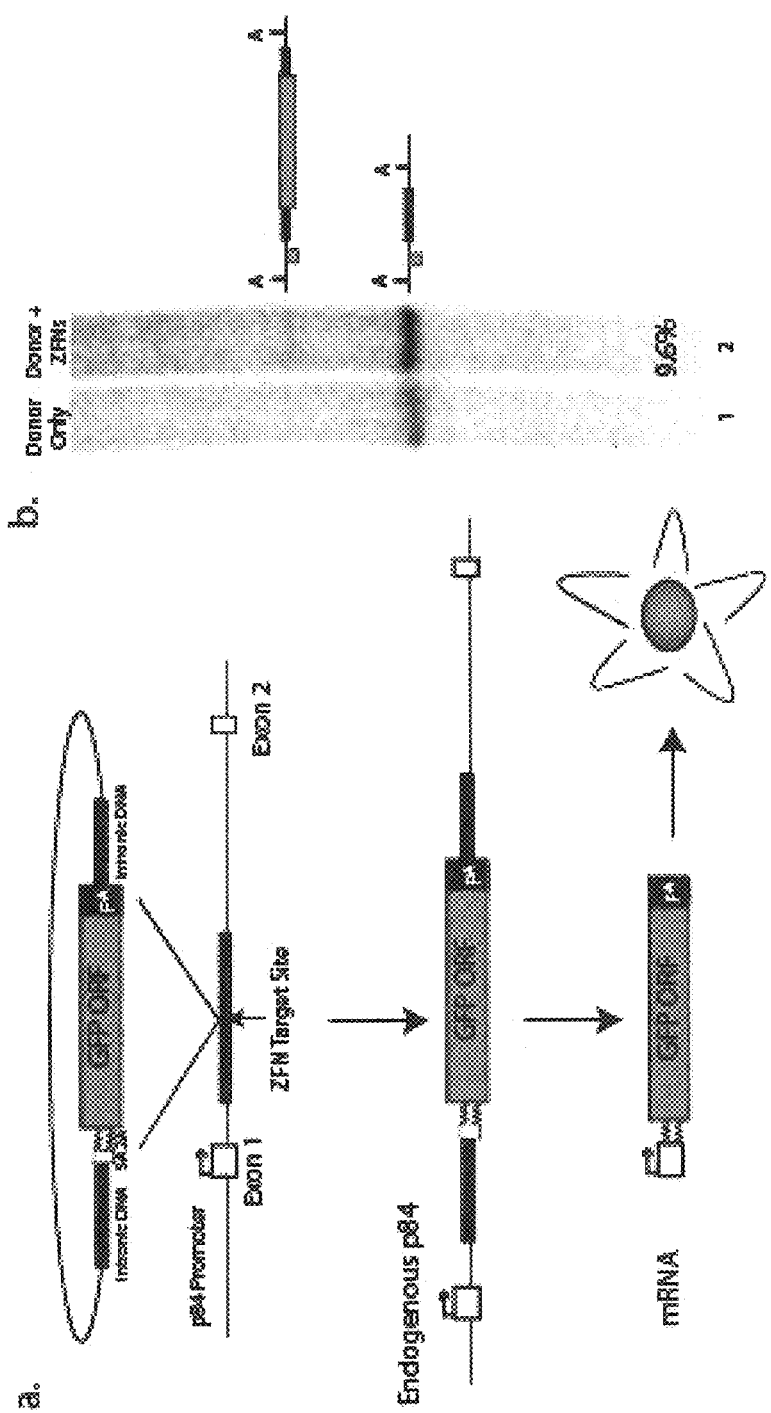
FIGS. 7A and 7B depict ZFN-mediated insertion of a promoterless GFP ORF.

Results are shown in FIGS. 3 and 4. Targeted integration frequency analysis (FIGS. 3A and B) demonstrated that integration of donor sequences into PPP1R12C was significantly increased in the presence of the ZFNs in both K562 (FIG. 3A) and 293T (FIG. 3B) cells. The results of the PCR analysis were verified by Southern blotting (see FIG. 7B).

Furthermore, as shown in FIG. 4, GFP expression by FACS analysis also confirmed that the GFP donor sequence was integrated into PPP1R12C. In particular, the donor GFP sequence integration frequency into PPP1R12C (FIG. 4A) without co-introduction of the ZFN expression construct was negligible. In the presence of the ZFNs, the percent of cells in which the donor sequence was integrated into the target site in PPP1R12C increased to 13.09% (FIG. 4B). Likewise, in 293T cells, the donor sequence was not integrated in wild-type cells (FIG. 4C, 0%) but was integrated in 3.66% of cells in the presence of PPP1R12C-targeted ZFNs (FIG. 4D). In Hep3B cells, the donor sequence integrated into 0.65% cells in the absence of PPP1R12C-targeted ZFNs (FIG. 4E) but was integrated into 1.73% of Hep3B cells in the presence of PPP1R12C-targeted ZFNs (FIG. 4F).

Thus, in a variety of cell types, ZFNs drove targeted integration of a promoterless exogenous coding sequence into the PPP1R12C "safe harbor" locus.

Example 3: Quantitative RT-PCR Measurement of PPP1R12C/p84 mRNA

Figure 5:
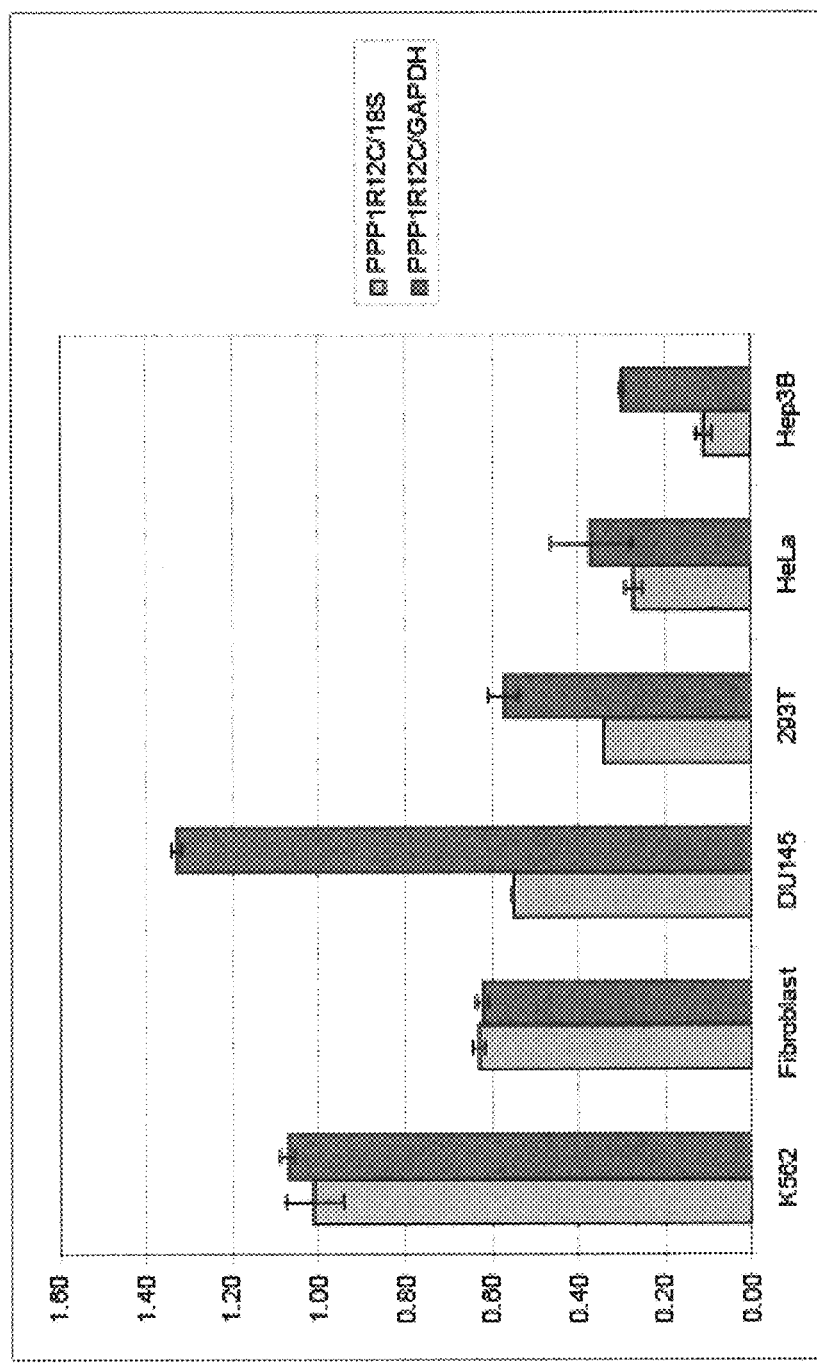
FIG. 5 is a graph depicting expression of PPP1R12C/p84 mRNA in the indicated cell types. PPP1R12C/18S indicates expression of the PPP1R12C locus relative to 18S, while PPP1R12C/GAPDH indicates expression relative to expression of GAPDH.

Quantitative RT-PCR measurement of PPP1R12C/p84 mRNA levels across a panel of commonly used transformed cell types (HEK293 (293T), fibroblasts, K562, HeLa, DU-145, Hep3B) was done to investigate if the gene was expressed in a variety of cell types. Results are presented as the ratio of expression of the PPP121R12C locus relative to either 18S or GAPDH. Briefly, levels of PPP1R12C mRNA were measured by real-time RT-PCR on an Applied Biosystems 7300 TaqMan machine as described in Tan et al. (2003) Proc. Nat'l Acad. Sci. USA 100:11997-12002), using a custom-made gene expression assay (ABI) for PPP1R12C. The results, shown in FIG. 5, demonstrated that PPP1R12C/p84 is broadly transcribed, in conformance with available data indicating that PPP1R12C/p84 is constitutively transcribed in all human cells/tissues studied.

Example 4: Targeted Integration into PPP1R12C Locus

To determine the utility of the PPP1R12C (p84) gene locus for gene addition, lead ZFNs from the panel of ZFNs shown in Table 1 were identified via a screen employing transient transfection of a panel of alternative ZFN designs and the Surveyor Nuclease Assay to determine the efficiency of DSB induction (Miller et al. (2007) Nat Biotechnol. 25(7):778-85). This assay measures the fraction of PPP1R12C/p84-derived chromatids carrying the genetic signature of DSB repair: small insertions and deletions generated by non-homologous end-joining. For all experiments on targeted integration into PPP1R12C/p84, we used a 1.6 kb donor DNA construct homologous to the chromosomal locus (Urnov et al., Nature. 2005 435(7042):646-51), and introduced heterologous stretches described using standard recombinant DNA techniques. An autonomous expression cassette for the ΔLNGFR cell surface marker was introduced outside the right homology arm of the donor construct using a unique SnaBI site. HEK293 and K562 cells were cultured and transfected with DNA constructs as described in Urnov et al. (ibid).

Figure 6:
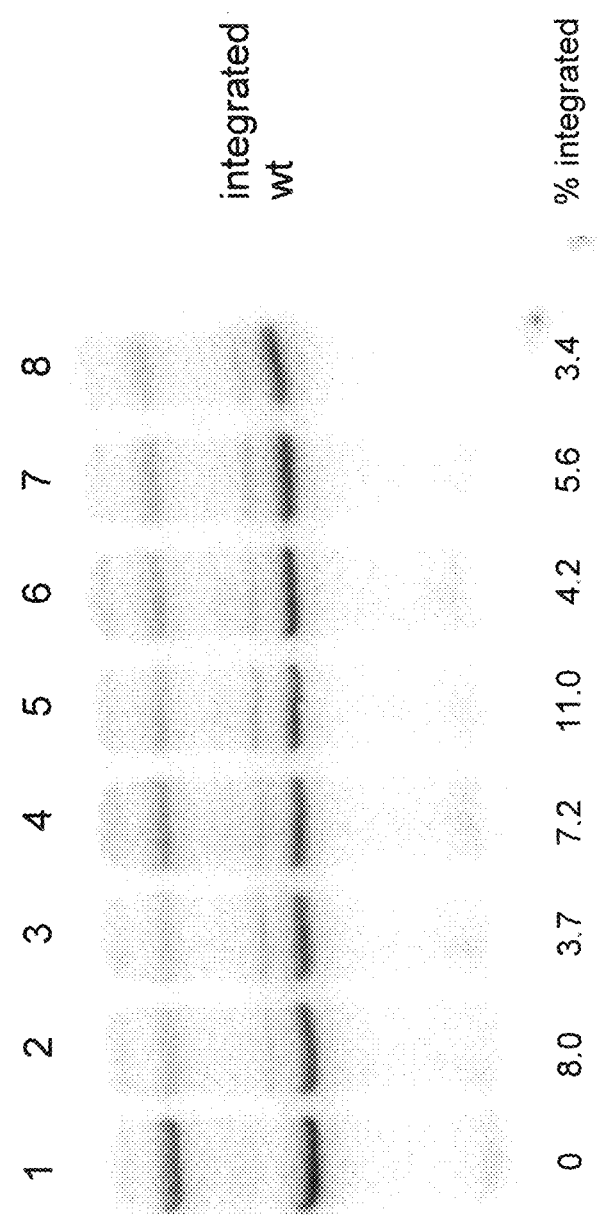
FIG. 6 depicts integration of a donor polynucleotide into the PPP1R12C/p84 locus in the presence or absence of the indicated ZFNs. The percent integration is shown beneath each lane. Lane 1 shows the negative control (no ZFN). Lane 2 shows cells transfected with ZFN pair 15554/15587; lane 3 shows cells transfected with ZFN pair 15554/15590; lane 4 shows cells transfected with ZFN pair 15556/15587; lane 5 shows cells transfected with ZFN pair 15556/15590; lane 6 shows cells transfected with ZFN pair 15557/15587; lane 7 shows cells transfected with ZFN pair 15557/15590; and lane 8 shows cells transfected with ZFN pair 9931/10099. ZFN pairs are shown in Table 1.

As shown in FIG. 6, all ZFN pairs tested integrated the donor construct, as compared to the negative control which showed no integration. These data demonstrated that ZFNs efficiently targeting a DSB into the desired region of PPP1R12C/p84 gene locus have been obtained.

In addition, the lead ZFN pair (15556/15590, lane 5 of FIG. 6) identified in this assay introduced a DSB ~1,800 bp downstream of the transcription start site of the PPP1R12C/p84 gene i.e. sufficiently distant from the native promoter sequences to permit a promoter-free donor DNA design for the addition of an open reading frame to this locus (FIG. 7A). We have shown previously that optimization of the ZFPs targeting a DNA site increases genome editing rates. See, e.g., Urnov et al. (2005). In agreement with this observation, optimization of the lead ZFNs for PPP1R12C/p84 also resulted in a marked enhancement (~4-fold increase) in cleavage activity resulting in a population of transiently transfected K562 cells displaying one edited chromatid in five.

Example 5: ZFN-Mediated Site-Specific Gene Addition

To determine whether the ZFNs above would drive efficient site-specific addition of a gene cassette into the PPP1R12C/p84 locus, we used a promoterless donor DNA design that exploited the native PPP1R12C/p84 promoter to yield a marker-positive cell (FIG. 7a). This donor plasmid includes two 750 bp stretches of sequence homologous to the region flanking the DSB site in intron 1 of the PPP1R12C/p84 locus interrupted by a promoterless GFP ORF and polyadenylation signal sequence. As exon 1 of PPP1R12C/p84 is translated, to achieve native PPP1R12C/p84 promoter driven GFP expression we included a splice acceptor site followed by the 2A ribosome stuttering signal (see, Fang et al (2005) *Nat Biotech.* 23:584), upstream of the ORF (FIG. 7A).

As depicted in FIG. 7A, bona fide site-specific gene addition of this cassette into the PPP1R12C/p84 locus would result in a single transcript driven from the PPP1R12C/p84 promoter that includes exon 1 of PPP1R12C/p84 and the marker GFP ORF. Translation of this mRNA would result in the generation of 2 separate polypeptides as a result of the 2A peptide sequence; (i) the peptide encoded by exon 1 of PPP1R12C/p84; and (ii) a complete GFP polypeptide. FACS analysis was performed using a bench top mini-FACS device (Guava Technologies) and the data was further analyzed using the WinMDI software. DNA-based analysis of targeted integration frequency was performed by a highly quantitative PCR assay as described (Urnov et al., 2005), except the restriction enzyme digestion step was omitted (the sole exception being experiments with a donor that introduces a 30 bp patch that contains a NcoI recognition site, in which the small size difference between a wild-type and integrant-carrying chromosome necessitated the use of restriction enzyme digestion). Southern blotting on genomic DNA digested with DpnI to eliminate excess donor DNA and AccI to digest the genomic DNA was performed as described (Urnov et al., 2005). Genome-wide expression profiling and immunocytochemistry were performed as described essentially in Miller et al. (2007) *Nat. Biotechnol.* 25(7):778-785 and Tan et al. (2003) *Proc Natl Acad Sci USA* 100:11997-12002.

Analysis of K562 cells 48 hrs post-transfection with plasmid DNAs encoding the ZFN and donor DNA constructs demonstrated that, on average, 10% of chromatids in the cell population had acquired the donor-specified cassette as gauged by PCR and by Southern blotting (FIG. 7B). The modified cells were then grown for a month (over 30 population doublings), in the absence of any selection. Consistent with the molecular data obtained at day 2 (FIG. 7B, lane 2), and despite an extended period in culture, 13% GFP-positive cells were observed in the ZFN and donor treated pool, while less than 1% of the cells treated with the donor plasmid alone expressed GFP. These data show that addition of a promotorless marker ORF to the human PPP1R12C/p84 locus yields a high frequency of stably marker-positive cells in the absence of selection for the desired event.

To determine the generality of these observations, we conducted an analogous experiment with two additional commonly used cell types of distinct derivation (HEK293, a cell line obtained by adenovirus transformation of neuronal cells, and Hep3B, a hepatocellular carcinoma). Noting that the endogenous PPP1R12C/p84 promoter is active both these cell types, we used the same promotorless GFP donor plasmid as before (FIG. 7A, top panel) and were able to obtain pools of GFP-positive cells carrying a ZFN-added ORF at the PPP1R12C/p84 4 locus. Notably, other than the use of transient transfection conditions specific for the cell type of interest, no other modification was necessary for the reagents to perform GFP ORF addition.

Taken together, these data demonstrate that ZFN-mediated site-specific stable gene addition to the PPP1R12C/p84 gene locus can be rapidly achieved by simple transient transfection of appropriate plasmid DNAs across a panel of commonly used human cells.

Example 6: Gene Addition to PPP1R12C/p84 Results in Stable Expression Levels

Transgenesis via random integration of foreign DNA via plasmid or viral delivery often results in variable initial gene expression levels as well as instability of expression over time.

Figure 8B:
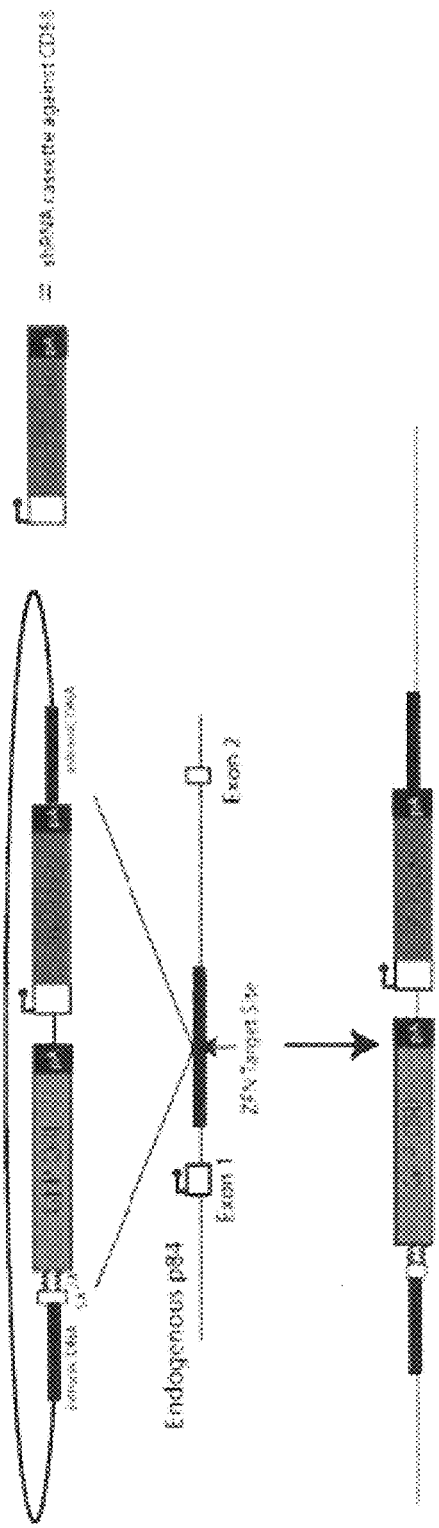

To determine whether ZFN-mediated site specific gene addition to the PPP1R12C/p84 locus would overcome these limitations, we exposed K562 cells to the ZFN and GFP ORF-encoding plasmids, expanded the cells in the absence of any selective agent for 4 weeks, and then used FACS to isolate the GFP-positive cell pool. PCR amplification of the larger (transgene-containing) chromatid is less efficient than that of the smaller, wild-type allele in a mixed cell population. Normalizing for this difference we genotyped the PPP1R12C/p84 locus in these cells by PCR, which revealed that ~80% of the chromatids carry the inserted ORF at the PPP1R12C/p84 gene locus (FIG. 8E, lane 2). Importantly, limiting dilution without additional sorting for GFP expression generated a panel of ~20 single cell-derived clonal lines found carry the precise insertion of the GFP cassette at PPP1R12C/p84 in a monoallelic or diallelic configuration, and at a relative frequency fully consistent with results of the PCR genotyping.

In addition, sequence-based genotyping of the transgenic chromatids revealed the precise, homology-based addition of the donor-specified transgene to the PPP1R12C/p84 locus.

To determine the stability of GFP expression, representative control K562 cells, the GFP-positive FACS enriched cell pool, and two single-cell clonal lines, monoallelic and diallelic for GFP insertion at PPP1R12C/p84, were grown for 50 cell doublings, and assayed for GFP expression level biweekly. The data, shown in FIG. 8A, revealed (i) no loss of mean fluorescence intensity over course of the experiment; (ii) no change in the overall fraction of marker-negative cells in the GFP-positive cell pool (~5%); and (iii) a consistently higher mean fluorescence intensity of cells homozygous for the GFP cassette at PPP1R12C/p84 than heterozygous.

These data demonstrate that ZFN-enabled ORF addition to the PPP1R12C/p84 gene locus results in the long-term stability and consistency of expression expected from engineering an "endogenous promoter trap."

Example 7: ZFN-Driven Addition of an Autonomous Expression Cassette

To extend the results obtained with the promoterless GFP ORF system for marker expression driven by the PPP1R12C/p84 promoter (FIG. 7), we next evaluated the feasibility of using a donor DNA design that encodes an autonomous expression cassette: this so-called "promoter-transcription unit" (PTU) carries its own promoter, followed by a stretch to be transcribed (such as a shRNA-encoding construct or a cDNA), and a transcription termination signal (e.g., a poly(A) stretch or an RNA polymerase III terminator). We modified our donor plasmid to contain an expression cassette for an shRNA. This donor DNA design is shown in schematic form in FIG. 8B. We chose to retain the elements of promoterless GFP ORF system as a method of tagging cells that have undergone bona fide gene addition to the PPP1R12C/p84 locus. Downstream of the GFP cassette we included a shRNA expression cassette targeting the cell surface marker CD58, (known to be expressed in K562 cells), thus physically linking GFP expression (driven from PPP1R12C/p84) to the integration of the shRNA expression construct at the same locus.

Quantitative PCR analysis 48 hrs post-transfection of K562 cells with the ZFNs and the shRNA-containing donor plasmid revealed 8% of the PPP1R12C/p84 chromatids to have acquired the ORF-PTU cassette at the target site. FACS sorting of the GFP-positive cell pool resulted in a ~10-fold enrichment in ZFN-modified chromatids (FIG. 8D).

Figure 8C:
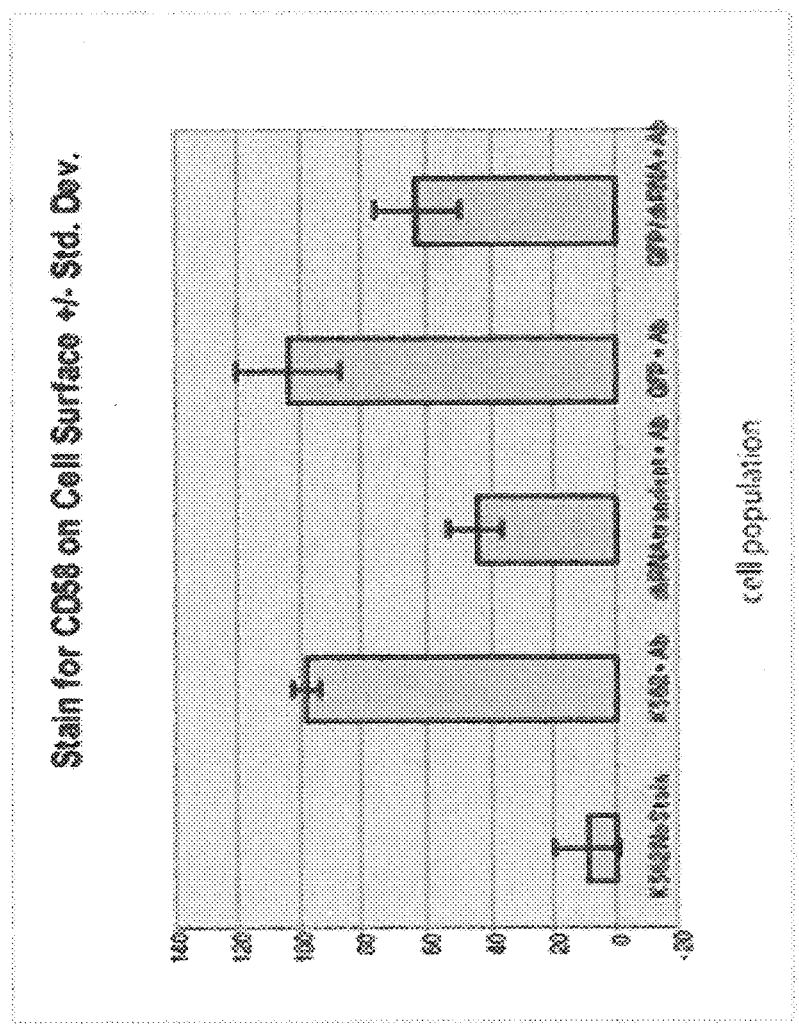

To determine the efficacy of the inserted shRNA cassette we compared control cells and PPP1R12C/p84 ZFN/donor modified cells by FACS staining for CD58, the target of the shRNA molecule. Importantly, cell-surface staining for CD58 was significantly reduced even after 30 cell population doublings and was comparable in magnitude to that seen 48 hrs post-transient transfection with the shRNA expression plasmid itself. See, FIG. 8C. It is noteworthy that the 48 hr, transient-transfection sample demonstrates target gene reduction comparable to that seen in cells carrying only 1 or 2 copies in a stably transgenic setting. Parallel generation of a pool of ZFN-modified cells using the GFP only donor (i.e. site-specific gene addition but no shRNA cassette) resulted in normal levels of CD58 staining, while a control sample in which the CD58 antibody was omitted provided for only residual fluorescence.

Taken together, these data demonstrate the utility of the promoterless GFP-linked PTU donor system for the rapid, drug-selection-free, single-step tagging and isolation of a cell population transgenic at a specific site for a stably expressed PTU.

Example 8: Specificity of ZFN-Driven PPP1R12C/p84 Gene Targeting

We used two well-established assays to experimentally investigate the specificity of ZFN-driven gene addition using plasmid based delivery.

First, we measured the generation of DSBs genome-wide using a well-studied hallmark of DSB repair, namely the assembly of a focus of phosphorylated histone variant H2A.X at the repair site (Paull et al. (2000) *Curr Biol* 10:886-895). We conducted these assays conducted in parallel with positive control ZFNs (targeting the IL2Rγ locus). The PPP1R12C/p84- and IL2Rγ-targeting ZFN employ high-fidelity "obligate heterodimer" forms of the FokI endonuclease, designed to limit the action of the pair of ZFNs to their required target. See, Miller et al. (2007) *Nat. Biotechnol.* 25(7):778-785. In the case of these IL2Rγ-targeting ZFNs this results in proteins that generate only a single DSB above background in the whole nucleus.

Figure 9A:
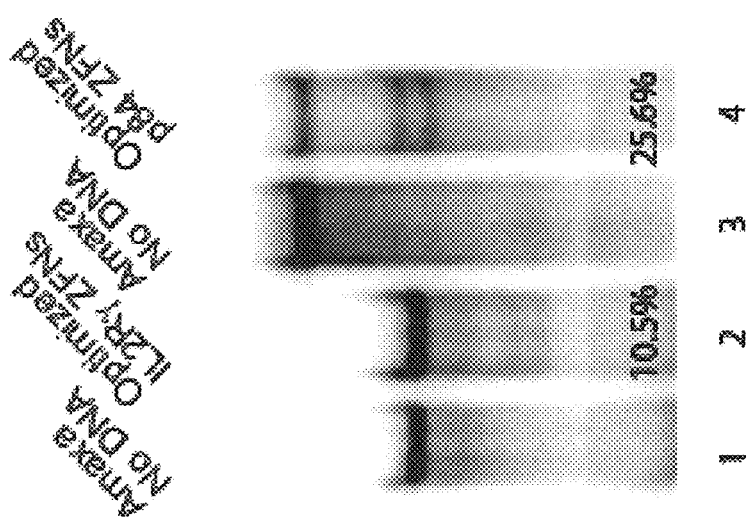
FIGS. 9A and 9B depict nucleus-wide molecular cytological survey of ZFN action.
Figure 9B:
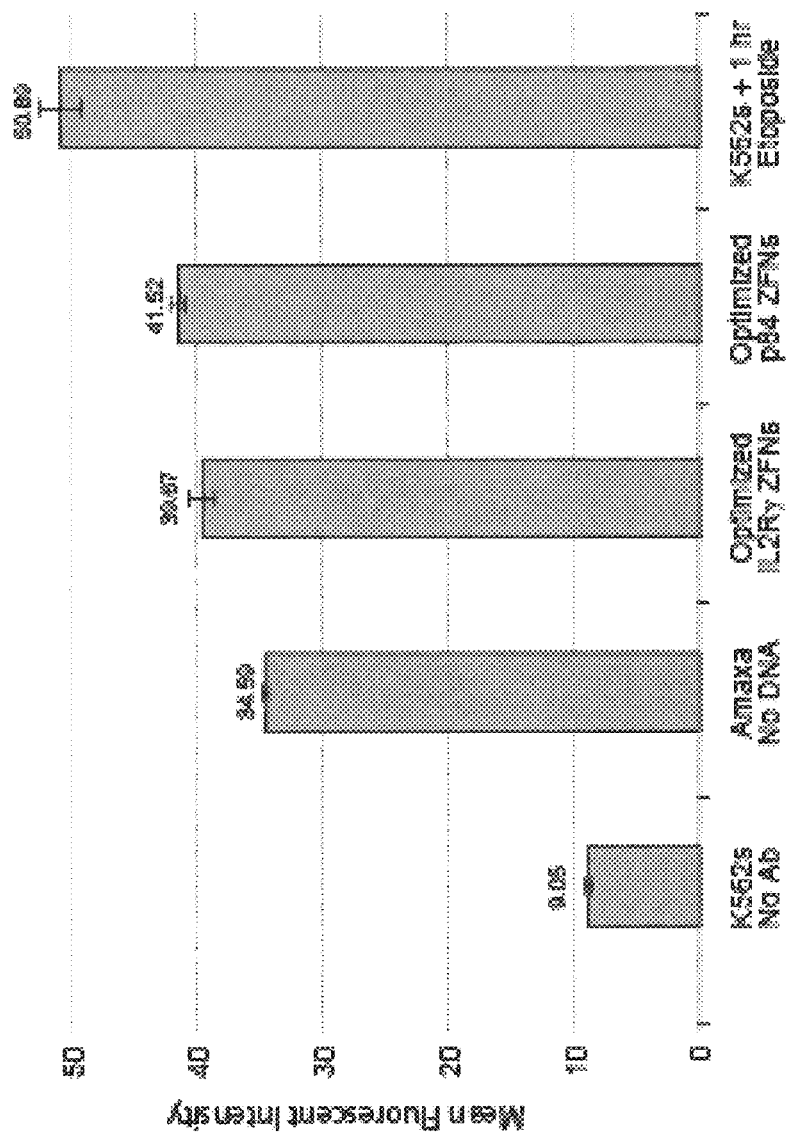

Despite being ~2.5× more effective at editing their intended target site, the PPP1R12C/p84 ZFNs showed statistically indistinguishable levels of H2A.X staining from those obtained with the IL2Rγ-targeting ZFNs. See, FIGS. 9A and 9B. In contrast, treatment with the DSB-inducing drug etoposide resulted in a statistically significant increase in H2A.X signal, thus confirming assay functionality.

Second, we asked whether the expression of the PPP1R12C/p84 ZFNs would increase the rate at which the donor DNA became randomly integrated into the genome. To address this question, we used a plasmid donor DNA carrying an autonomous expression cassette for a cell surface marker (ΔNGFR) placed outside the donor homology arms, essentially as described in Moehle et al. (2007). Misintergation of the plasmid would result in the incorporation and expression of the ΔNGFR cassette, which homology-directed repair results in GFP positive cells without ΔNGFR expression.

In agreement with earlier work examining the ZFNs targeted to the IL2Rγ locus (Moehle et al., 2007; Urnov et al., 2005), we found no increase in donor plasmid misintegration rate above that observed in cells treated with the donor DNA only. In contrast, the addition of etoposide (a DNA damage inducing drug) lead to a statistically significant increase in the number of ΔNGFR cells.

These data indicate that the PPP1R12C/p84-directed nucleases do not, within the limit of sensitivity of the assays used, generate more than a single DSB above background, nor drive a measurable increase in donor plasmid random integration. Thus, in two assays of ZFN specificity—a direct measurement of the number of ZFN-induced DSBs per genome and an indirect readout via random integration—the PPP1R12C/p84 ZFNs demonstrated high specificity, supporting their use in the generation of transformed human cell lines.

All patents, patent applications and publications mentioned herein are hereby incorporated by reference, in their entireties, for all purposes.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A composition comprising:
   one or more polynucleotides encoding one or more nucleases, each nuclease comprising (i) a DNA-binding domain and (ii) a cleavage domain or cleavage half-domain, wherein the DNA-binding domain has been engineered to bind to a first target site in intron 1 of a PPP1R12C gene in the genome of an isolated cell.

2. The composition of claim 1, wherein the one or more polynucleotides encode at least two nucleases.

3. The composition of claim 1, further comprising an isolated nucleic acid sequence.

4. The composition of claim 3, wherein the isolated nucleic acid sequence encodes a polypeptide.

5. The composition according to claim 4, wherein the polypeptide is selected from the group consisting of an antibody, an antigen, an enzyme, a growth factor, a cell surface receptor, a nuclear receptor, a hormone, a lymphokine, a cytokine, a reporter, functional fragments thereof and combinations thereof.

6. The composition of claim 5, wherein the reporter comprises GFP.

7. The composition of claim 3, wherein the polynucleotide is selected from the group consisting of one or more shRNAs, one or more RNAi molecules, one or more miRNAs and combinations thereof.

8. The composition of claim 3, wherein the isolate nucleic acid sequence further comprises a promoter.

9. The composition of claim 3, wherein the isolated nucleic acid sequence does not comprise a promoter.

10. The composition of claim 3, wherein the isolated nucleic acid sequence further comprises a first nucleotide sequence that is homologous but non-identical to a first sequence in the PPP1R12C gene.

11. The composition of claim 10, wherein the isolated nucleic acid sequence further comprises a second nucleotide sequence that is homologous but non-identical to a second sequence in the PPP1R12C gene.

12. The composition of claim 10, wherein the isolated nucleic acid sequence comprises a tandem cassette.

13. The composition of claim 3, wherein the isolated nucleic acid sequence is a plasmid.

14. The composition of claim 3, wherein the isolated nucleic acid sequence is a linear DNA molecule.

15. The composition of claim 1, wherein the cleavage half-domains are from a Type IIS restriction endonuclease.

16. The composition of claim 15, wherein the Type IIS restriction endonuclease is selected from the group consisting of FokI and StsI.

17. The composition of claim 1, wherein at least one of the cleavage half-domains comprises an alteration in the amino acid sequence of a dimerization interface of the cleavage half-domain.

18. The composition of claim 1, wherein the polynucleotide is within an isolated cell.

19. The composition of claim 18, wherein the cell is a stem cell.

20. The composition of claim 19, wherein the stem cell is a hematopoietic stem cell.

* * * * *